United States Patent [19]
Eriksson et al.

[11] Patent Number: 5,972,646
[45] Date of Patent: *Oct. 26, 1999

[54] ISOLATED NUCLEIC ACID MOLECULE WHICH CODES FOR A 32 KDA PROTEIN HAVING 11-CIS RETINOL DEHYDROGENASE ACTIVITY, AND WHICH ASSOCIATES WITH P63, A PORTION OF A RETINOL BINDING PROTEIN RECEPTOR

[75] Inventors: Ulf Eriksson; Andras Simon; Anna Romert, all of Stockholm, Sweden

[73] Assignee: Ludwig Institute for Cancer Research, New York, N.Y.

[*] Notice: This patent is subject to a terminal disclaimer.

[21] Appl. No.: 08/562,114

[22] Filed: Nov. 22, 1995

Related U.S. Application Data

[63] Continuation of application No. 08/375,962, Jan. 20, 1995, Pat. No. 5,731,195, which is a continuation-in-part of application No. 08/258,418, Jun. 10, 1994, abandoned.

[51] Int. Cl.⁶ ............................ C12N 15/12; C12N 15/52; C12N 15/63; C12N 5/10
[52] U.S. Cl. ................... 435/69.1; 435/325; 435/320.1; 536/23.5
[58] Field of Search .............................. 435/69.1, 320.1, 435/252.3, 325; 536/23.1, 23.5, 24.3

[56] References Cited

U.S. PATENT DOCUMENTS 5,508,164  4/1996  Kausch et al. .................. 435/6

FOREIGN PATENT DOCUMENTS

WO23538  of 1993  WIPO.

OTHER PUBLICATIONS

Bavik et al., *J. Biol. Chem*, vol. 267, pp. 20540–20546 (1993).
Lied et al., *Trends Genet.*, vol. 17, pp. 427–433 (1992).
Mangelsdorf et al., *Genes Dev.*, vol. 6, pp. 329–344 (1992).
Bavik et al., *J. Biol. Chem.*, vol. 267, pp. 23035–23042 (1992).
Bavik et al., *J. Biol. Chem.*, vol. 266, pp. 14978–14985 (1991).
Posch et al., *Biochem.*, vol. 30, pp. 6224–6230 (1991).
Mangelsdorf et al., *Nature*, vol. 345, pp. 224–229 (1990).
Zelent et al., *Nature*, vol. 339 pp. 714–717 (1989).
Benbrook et al., *Nature*, vol. 333, pp. 669–672 (1988).
Brand et al., *Nature*, vol. 332, pp. 850–853 (1988).
Giguere et al., *Nature*, vol. 330, pp. 624–629 (1987).
Petkovich et al., *Nature*, vol. 330, pp. 440–450 (1987).
Bridges, *The Retinoids*, vol. 2, pp. 125–176 (1984).
Goodman et al., *The Retinoids*, vol. 2, pp. 41–88 (1984).
Alder et al., *Biochem. Biophys. Res. Commun.*, vol. 108, pp. 1601–1608 (1982).
Lai et al., *Nature*, vol. 298, pp. 848–849 (1982).
Inu et al., *Vision Res.*, vol. 22, pp. 1457–1468 (1982).
Zimmerman et al., *Exp. Eye Res.*, vol. 23, pp. 159–164 (1976).
Bok et al., *Exp. Eye Res.*, vol. 22, pp. 395–402 (1976).
Lion et al., *Biochem. Biophys. Acta.*, vol. 384, pp. 283–292 (1975).
Zimmerman et al., *Exp. Eye Res.*, vol. 21, pp. 325–332 (1975).
Heller et al., *J. Biol. Chem.*, vol. 250, pp. 3613–3619 (1975).
Wallace et al. (1987) Methods in Enzymology 152 : 432–442.
Bowie et al. (1990) Science 247 : 1307–1310.
Simon et al. (1995) J. Biol. Chem. 270 : 1107–1112.
Chai et al. (1995) J. Biol. Chem. 270 : 3900–3904.

*Primary Examiner*—Lila Feisee
*Assistant Examiner*—Michael Pak
*Attorney, Agent, or Firm*—Fulbright & Jaworski, LLP.

[57] ABSTRACT

In accordance with this invention, an RPE cell membrane associated protein which has a molecular weight of about 32 kd, as determined by SDS-PAGE, has been discovered. This protein, referred to an "p32," forms an oligomeric protein complex with the previously characterized p63 protein, a component of the membrane receptor for RBP. A nucleic acid molecule which codes for the p32 protein has also been isolated and sequence analysis shows that the p32 protein belongs to the family of short chain alcohol dehydrogenases, and exhibits 11-cis retinol dehydrogenase activity, the enzyme which catalyzes conversion of 11-cis-retinol into 11-cis retinaldehyde.

12 Claims, 7 Drawing Sheets

FIG. 3

```
   1                                    AGCTTTCCCCTGAGGAGGTCACCTGGGCTCCAGCC

Met Trp Leu Pro Leu Leu Leu Gly Val Leu Leu Trp Ala Ala Leu Trp Leu    17
  36   ATG TGG CTG CCT CTG CTG CTG GGT GTC TTG CTC TGG GCA GCA CTG TGG TTG

Leu Arg Asp Arg Gln Cys Leu Pro Ala Ser Asp Ala Phe Ile Phe Ile Thr    34
  88   CTC AGG GAC CGG CAG TGC CTG CCA GCC AGC GAT GCC TTT ATC TTC ATC ACC

Gly Cys Asp Ser Gly Phe Gly Arg Leu Leu Ala Leu Arg Leu Asp Gln Arg    51
 139   GGC TGT GAC TCG GGC TTT GGG CGG CTC CTT GCT CTG AGG CTG GAC CAG AGA

Gly Phe Arg Val Leu Ala Ser Cys Leu Thr Pro Ser Gly Ala Glu Asp Leu    68
 190   GGC TTC CGA GTA CTG GCC AGC TGC CTG ACA CCC TCG GGG GCG GAG GAC CTC

Gln Arg Val Ala Ser Ser Arg Leu His Thr Thr Leu Leu Asp Val Thr Asp    85
 241   CAG CGG GTC GCC TCC TCC CGC CTC CAC ACC ACC CTG CTG GAT GTC ACA GAT

Pro Gln Ser Ile Arg Gln Ala Val Lys Trp Val Glu Thr His Val Gly Glu   102
 292   CCC CAG AGC ATC CGG CAG GCA GTC AAG TGG GTG GAA ACG CAT GTT GGG GAA

Ala Gly Leu Phe Gly Leu Val Asn Asn Ala Gly Val Ala Gly Ile Ile Gly   119
 343   GCA GGG CTT TTT GGT CTG GTG AAT AAT GCT GGT GTG GCT GGC ATC ATT GGT

Pro Thr Pro Trp Gln Thr Arg Glu Asp Phe Gln Arg Val Leu Asn Val Asn   136
 394   CCC ACC CCA TGG CAG ACG CGG GAG GAC TTC CAG CGG GTG CTG AAT GTG AAC

Thr Leu Gly Pro Ile Gly Val Thr Leu Ala Leu Leu Pro Leu Leu Leu Gln   153
 445   ACG CTG GGT CCC ATC GGG GTC ACC CTC GCC CTG CTG CCC CTG CTG CTG CAG

Ala Arg Gly Arg Val Ile Asn Ile Thr Ser Val Leu Gly Arg Leu Ala Ala   170
 496   GCC CGG GGC CGA GTG ATC AAC ATC ACC AGT GTC CTT GGC CGT CTG GCA GCC

Asn Gly Gly Gly Tyr Cys Val Ser Lys Phe Gly Leu Glu Ala Phe Ser Asp   187
 547   AAT GGA GGG GGC TAC TGC GTC TCC AAG TTT GGC GTC GAG GCC TTC TCT GAC

Ser Leu Arg Arg Asp Val Ala Pro Phe Gly Val Arg Val Ser Ile Val Glu   204
 598   AGC CTG AGG CGA GAT GTG GCT CCT TTT GGG GTA CGG GTC TCT ATC GTG GAA

Pro Gly Phe Phe Arg Thr Pro Val Thr Asn Leu Glu Thr Leu Glu Asp Thr   221
 649   CCT GGC TTC TTC CGA ACC CCT GTG ACA AAC CTG GAA ACT TTG GAG GAC ACC

Leu Gln Ala Cys Trp Ala Arg Leu Pro Pro Ala Thr Gln Ala Leu Tyr Gly   238
 700   CTG CAG GCC TGC TGG GCA CGG CTG CCT CCA GCC ACA CAG GCC CTC TAT GGG

Glu Ala Phe Leu Thr Lys Tyr Leu Arg Val Gln Gln Arg Ile Met Asn Met   255
 751   GAG GCC TTC CTC ACC AAA TAC CTG AGA GTG CAG CAA CGT ATC ATG AAC ATG

Ile Cys Asp Pro Asp Leu Ala Lys Val Ser Arg Cys Leu Glu His Ala Leu   272
 802   ATC TGT GAT CCG GAC CTG GCC AAG GTG AGC AGG TGC CTG GAG CAT GCC CTA

Thr Ala Arg His Pro Arg Thr Arg Tyr Ser Pro Gly Trp Asp Ala Lys Leu   289
 853   ACT GCC CGT CAC CCC AGA ACC CGC TAC AGC CCA GGC TGG GAT GCC AAG CTG

Leu Trp Leu Pro Ala Ser Tyr Leu Pro Ala Arg Leu Val Asp Ala Val Leu   306
 904   CTC TGG TTG CCA GCC TCC TAC TTG CCA GCC AGG CTG GTG GAT GCT GTG CTC

Ala Trp Val Leu Pro Lys Pro Ala Gln Thr Val Tyr Stop                  318
 955   GCC TGG GTC CTT CCC AAG CCT GCC CAG ACA GTC TAC TAA ATCCAGCCCTCCAGC

1009   AAAAGATGGTTGTTCAAGGCAAGGACTCTGATTTATTCTGTCCCCTACCCTGGTACTGCCTGGTGTG

1076   TGGCATAAAACAGTCACTCAATAAATGTATTATTCAAAACAAAAAAA
```

FIG. 4

```
       1                                                                    50
p32    ..........  ..........  ........MW  LPLLLGVLLW  AALWLLRDRQ
BDH    MMLAARLSRP  LSQLPGKALS  VCDRENGTRH  TLLFYPASFS  PDTRRTYTSQ
FABG   ..........  ..........  ..........  ..........  ..........
EDH    ..........  ..........  ..........  ..........  ..........

51                                                                  100
p32    CLPASDAFIF  ITGCDSGFGR  LLALRLD...  QRGFRVLASC  L....TP...
BDH    ADAASGKAVL  VTGCDSGFGF  SLAKHLH...  SKGFLVFAGC  LLKEQGD...
FABG   .MNFEGKIAL  VTGASRGIGR  AIAETLA...  ARGGKVIGTA  ....TSE...
EDH    ....ARTVVL  ITGCSSGIGL  HLAVRLASDP  SQSFKVYATL  RDLKTQGRLW 101                                                                 150
p32    SGAEDLQRVA  SSRLHTTLLD  VTDPQSIRQA  VKWVETHV..  GEAGLFGLVN
BDH    AGVRELDSLK  SDRLRTIQLN  VCNSEEVEKA  VETVRSGLKD  PEKGMWGLVN
FABG   NGAQAISDYL  GANGKGLMLN  VTDPASIESV  LEKIRAEFGE  VDI....LVN
EDH    EAARALA.CP  PGSLETLQLD  VRDSKSVAAA  RERVTEGRVD  V......LMC 151                                                                 200
p32    NAGVAGIIGP  TPWQTREDFQ  RVLNVNTLGP  IGVTLALLPL  LLQAR.GRVI
BDH    NAGIST.FGE  VEFTSMETYK  EVAEVNLWGT  VRTTKSFLPL  LRRAK.GRVV
FABG   NAGI.TRDNL  LMRMKDEEWN  DIIETNLSSV  FRLSKAVMRA  MMKKRHGRII
EDH    NAGL.GLLGP  LEALGEDAVA  SVLDVNVVGT  VRMLQAFLPD  MKRRGSGRVL

201                    ▽                                           250
P32    NITSVLGRLA  ANG.GGYCVS  KFGLEAFSDS  LRRDVAPFGV  RVSIVEPGFF
BDH    NISSMLGRMA  NPARSPYCIT  KFGVEAFSDC  LRYEMHPLGV  KVSVVEPGNF
FABG   TIGSVVGTMG  NGGQANYAAA  KAGLIGFSKS  LAREVASRGI  TVNVVAPGFI
EDH    VTGSVGGLMG  LPFNDVYCAS  KFALEGLCES  LAVLLLPFGV  HLSLIECGPV 251                                                                 300
p32    ..RT..PV..  TNLETLEDTL  QACWARL...  ..........  PPATQALYGE
BDH    IAAT..SL..  YSPERIQAIA  KKMWDEL...  ..........  PEVVRKDYGK
FABG   ETDMTRAL..  SDDQRAGILA  QVPAGRL...  ..........  GGAQEIANAV
EDH    HTAFMEKVLG  SPEEVLDRTD  IHTFHRFYQY  LAHSKQVFRE  AAQNPEEVAE 301                                                                 350
p32    AFLTKYLRVQ  QRIMNMICDP  DLAKVSRCLE  HALTARHPRT  RYSPGWDAKL
BDH    KYFDEKIAKM  ETYCN.SGST  DTSSVINAVT  HALTAATPYT  RYHPMDYYWW
FABG   AFLASDEAAY  ITGETLHVNG  GMYMV.....  ..........  ..........
EDH    VFLTALRAPK  PTLRYFTTER  FLPLLRMRLD  DPSGSNYVTA  MHREVFGDVP 351                                       389
P32    LWLPA.SYLP  ARLVDAVLAW  VLPKPAQTVY  ..........
BDH    LRMQVMTHFP  GAISDKIYIH  ..........  ..........
FABG   ..........  ..........  ..........  ..........
FDH    AKAEAGAEAG  GGAGPGAEDE  AGRSAVGDPE  LGDPPAAPQ
```

FIG. 5
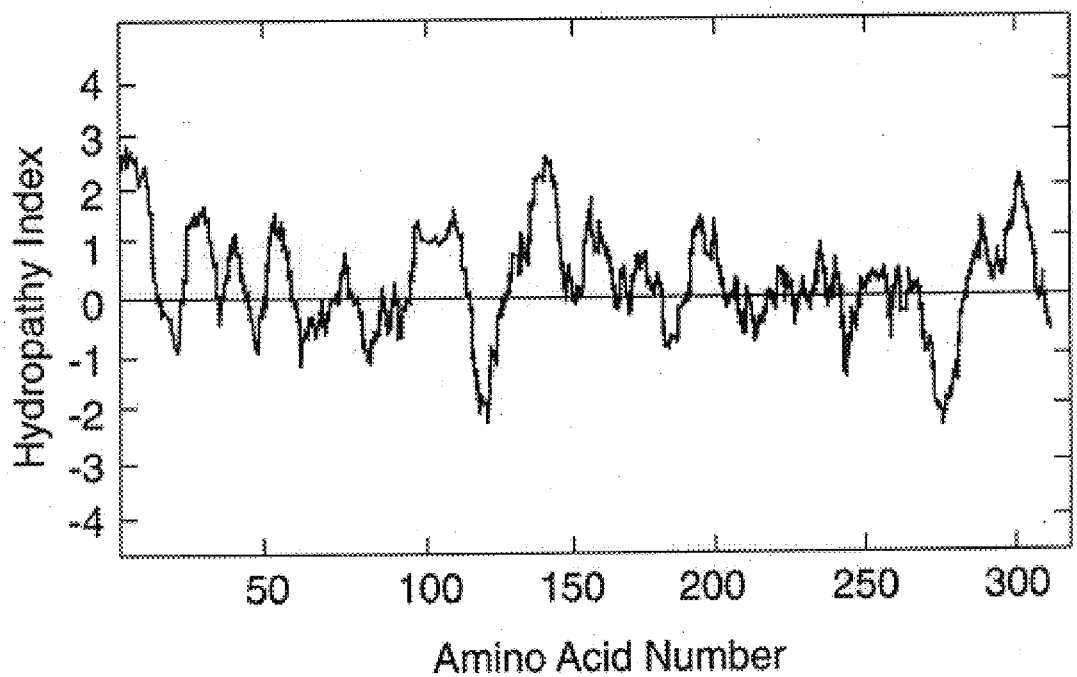
FIG. 6
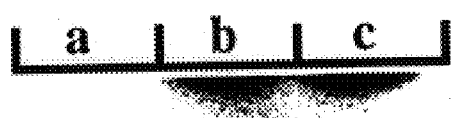
 — p32

- p32

ISOLATED NUCLEIC ACID MOLECULE WHICH CODES FOR A 32 KDA PROTEIN HAVING 11-CIS RETINOL DEHYDROGENASE ACTIVITY, AND WHICH ASSOCIATES WITH P63, A PORTION OF A RETINOL BINDING PROTEIN RECEPTOR

RELATED APPLICATIONS

This application is a continuation of application Ser. No. 08/375,962, filed Jan. 20, 1995, now U.S. Pat. No. 5,731,195, which is itself a continuation in part of application, Ser. No. 08/258,418 filed Jun. 10, 1994, now abandoned. Both applications are incorporated by reference.

FIELD OF THE INVENTION

This invention relates to a protein having 11-cis retinol dehydrogenase activity, and which forms a complex with a specific portion of a membrane receptor for plasma retinol-binding protein (RBP) expressed, e.g., in retinal pigment epithelium (RPE), and more specifically a 32 kDa protein having 11-cis retinol dehydrogenase activity, which forms a complex with a 63 kDa RBP-binding membrane protein. The invention also involves isolation of the 32 kDa protein (p32), as well as nucleic acid molecules coding for p32 or complimentary to coding sequences therefor, in addition to various applications of these materials.

BACKGROUND AND PRIOR ART

Retinoids (vitamin A-derivatives) have important physiological functions in a variety of biological processes. During embryonic growth and development, as well as during growth and differentiation of adult organisms, retinoids act as hormones and participate in the regulation of gene expression in a number of cell types. See Lied et al. Trends Genet., 17:427–433 (1992). It is believed that the effects of these molecules are mediated through two classes of nuclear ligand-controlled transcription factors, the retinoic acid receptors (RARs) and the retinoid X receptors (RXRs), Benbrook et al., Nature, 333:669–672 (1988); Brand et al., Nature, 332:850–853 (1988); Giguere et al., Nature, 330:624–629 (1987); Mangelsdorf et al., Nature, 345:224–229 (1990); Mangelsdorf, et al. Genes Dev. 6:329–344 (1992); Petkovich et al. Nature 330:440–450 (1987); and Zelent et al., Nature 339:714–717 (1989).

Apart from their role as hormones in cellular growth and differentiation, retinoids are also involved in the visual process as the stereo isomer 11-cis retinaldehyde of retinaldehyde is the chromophore of the visual pigments. See, e.g. Bridges, *The Retinoids*, Vol. 2, pp 125–176, Academic Press, Orlando, Fla., (1984).

Under normal physiological conditions most cells, both ocular and non-ocular, obtain all-trans retinol as their major source of retinoids. Despite the many different metabolic events taking place in different tissues, it is known that a common extracellular transport machinery for retinol has evolved. Specifically, in plasma, retinol is transported by plasma retinol binding protein (RBP). See Goodman et al., *The Retinoids*, Academic Press, Orlando Fla., Volume 2, pp. 41–88 (1984). The active derivatives of retinol, i.e., retinoic acid in non-ocular tissues and mostly 11-cis retinaldehyde for ocular tissues, are generated by cellular conversion of trans-retinol, using specific mechanisms. To date, none of these mechanisms have been fully defined at the molecular level and several of the enzymes involved have only been identified by enzymatic activities. See Lion et al., Biochem. Biophys. Acta. 384:283–292 (1975); Zimmermann et al., Exp. Eye Res. 21:325–332 (1975); Zimmermann, Exp. Eye Res. 23:159–164 (1976) and Posch et al., Biochemistry 30:6224–6230 (1991).

Polarized retinal pigment epithelial cells (polarized RPE) are unique with regard to retinoid uptake since all-trans retinol enters these cells via two different mechanisms. Retinol accumulated from RBP is taken up through the basolateral plasma membrane, while all-trans retinol, presumably taken up from the interstitial retinol-binding protein (IRBP) following bleaching of the visual pigments, may enter through the apical plasma membrane. See Bok et al., Exp. Eye Res. 22:395–402 (1976); Alder et al., Biochem. Biophys. Res. Commun. 108:1601–1608 (1982); Lai et al., Nature 298:848–849 (1982); and Inu et al., Vision Res. 22:1457–1468 (1982).

The transfer of retinol from REP to cells is not fully understood. In a number of cell types, including RPE, specific membrane receptors for RBP have been identified. This is consistent with a receptor-mediated uptake mechanism for retinol. For example isolated retinal binding protein receptors, nucleic acid molecules coding for these receptors and antibodies binding to the receptor have been taught, in references relating to the first of the two mechanisms. See Bavik et al., J. Biol. Chem. 266:14978–14985 (1991); Bavik, et al. J. Biol. Chem. 267:23035–23042 1992; Bavik et al., J. Biol. Chem. 267:20540–20546 (1993); and copending U.S. application Ser. No. 083,539 and International Publication WO 93/23538, all of which are incorporated by reference herein. See also Heller, J. Biol. Chem. 250:3613–3619 (1975); and Bok et al., Exp. Eye Res. 22:395–402 (1976).

Retinol uptake on the apical side of the RPE for the regeneration of 11-cis retinaldehyde, is less well characterized. Regardless of the origin of all-trans retinal, however, the synthesis and apical secretion of 11-cis retinaldehyde seems to be the major pathway for accumulated retinal in the RPE. At present, it is not known whether similar mechanisms are used with regard to cellular retinal uptake through the basolateral and the apical plasma membranes. Available data do show that functional receptors for RBP are exclusively expressed on the basolateral plasma membrane of RPE-cells. Bok et al., Exp. Eye Res. 22:395–402 (1976).

It is also known that RPEs express a 63 kDa protein (p63). This molecular weight, and all others, is by reference to SDS-PAGE, unless stated otherwise. It has also been shown by chemical cross-linking that this protein may be part of an oligomeric protein complex which functions as a membrane receptor for plasma retinol-binding protein (RBP) in RPEs, or a component of the retinoid uptake machinery in RPE cells. See Bavik et al, J. Biol. Chem. 266:14978–14875 (1991); Bavik et al., J. Biol, Chem. 267:23035–23042 (1992), U.S. patent application Ser. No. 083,539 and PCT application WO93/23538. The p63 protein has been isolated and the corresponding cDNA cloned. See Bavik et al., J. Biol. Chem. 267:20540–20546 (1993). Nothing in these references suggests the existence of the protein which is a feature of this invention.

SUMMARY OF THE INVENTION

In accordance with this invention, RPE membrane associated proteins which have a molecular weight of about 32 kd, as determined by SDS-PAGE, are disclosed. These proteins, referred to as "p32," form oligomeric protein complexes with the previously characterized p63 protein, a component of the membrane receptor for RBP. Also disclosed are nucleic acid molecules which code for the p32 protein. Sequence analysis shows that the p32 protein belongs to the family of short chain alcohol dehydrogenases, and exhibits 11-cis retinol dehydrogenase activity, the enzyme which catalyzes the stereospecific conversion of 11-cis retinol into 11-cis retinaldehyde in the presence of cofactor NAD+.

As will be shown, p32 has many important uses. For example, owing to its membrane bound 11-cis-retinol dehydrogenase activity, which catalyzes the conversion of 11-cis-retinol to 11-cis-retinaldehyde, a major metabolic step in retinoid metabolism in RPE-cells, retinoid accumulation and metabolism which may lead to retinitis pigmentosa, may be directly or indirectly tied to the presence of p32, and/or its activation or inhibition. As p32 has also been found to be a member of the short chain alcohol dehydrogenase super family, many known alcohol dehydrogenase inhibitors (and activators) are available to develop activity assays, and thus diagnostic materials for retinol uptake, and ocular retinoid metabolism.

Particular features of the invention include nucleic acid molecules which encode mammalian forms of these proteins, such as human, bovine, and murine forms. Also a part of the invention are probes, based upon extended sequences as described herein.

These and other aspects of this invention are more fully discussed in the following specification with accompanying drawings.

BRIEF DESCRIPTION OF THE FIGURES

FIG. 3 illustrates the nucleotide sequence of pλ321 and the deduced amino acid sequence of p32, with the partial amino acid sequences determined from peptides isolated from trypsin digested p32. Refer to SEQ. ID. NO:10

FIG. 4 illustrates amino acid sequence alignments of p32 and some related proteins belonging to the family of short-chain alcohol dehydrogenases. The sequence of these proteins are set forth in SEQ. ID. NO: 11 (rat D-b hydroxybutyrate dehydrogenase (rDBH)), SEQ. ID. NO: 12 (human estradiol 17-b dehydrogenase (hEDH)), SEQ. ID. NO: 13 (*E. Coli* 3-exoacyl [acyl carrier protein] reductase (FABg)), and SEQ. ID. No; 14 (p32).

FIG. 5 illustrates analysis of the amino acid sequence of p32.

FIG. 6 illustrates membrane interaction of p32 synthesized in vitro.

DETAILED DISCUSSION OF PREFERRED EMBODIMENTS

Figure 1A:
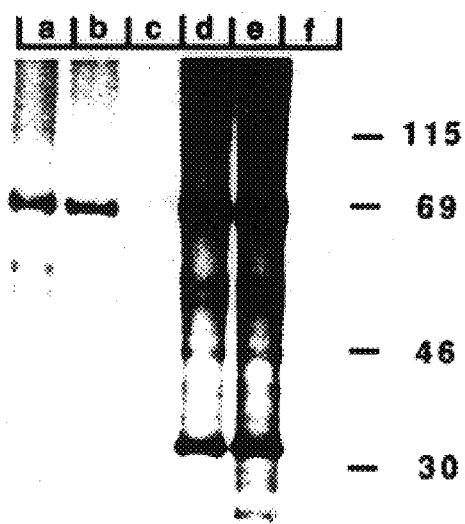
FIG. 1A shows SDS-PAGE analysis of radiolabeled protein from RPE-membranes and immunoprecipatation with mAb A52 against p63.

It is known that plasma retinol binding protein (RBP) can be chemically cross-linked to a high molecular weight complex of a 63 kDa protein (p63) receptor of retinal pigment epithelium membranes (RPE), forming an RBP-RBP receptor complex with elution properties of globular proteins of similar sizes having apparent molecular weights of approximately $M_r$ 150,000 and 450,000. See Bavik et al, J. Biol. Chem. 266:14978–14875 (1991), and Bavik et al., J. Biol. Chem. 267:23035–23042 (1992). The protein responsible for binding of RBP, expression of which is restricted to RPE, has been identified as a 63 kDa protein (p63). Through the generation of a monoclonal antibody A52 (mAb A52) to the 63 kDa protein which binds the RBP-RBP receptor complex and p63, and immunoaffinity chromatographic analysis, it has been found that the majority of p63 elutes as a monomer, with a significant portion of the protein found in positions corresponding to higher molecular weight species. This indicates that p63 exists in an oligomeric protein complex with other protein components. Bavik et al., J. Biol. Chem. 266:14978–14985 (1991), and Bavik et al, J. Biol. Chem. 267:23035–23042 (1992). Therefore, the following procedure was carried out to investigate the molecular characteristics of such oligomeric protein complexes, and whether p63 forms a complex with other proteins specific to RPE. The results show that a 32 kDa membrane associated protein (p32) indeed forms a complex with p63.

EXAMPLE 1

Bovine RPE-cells were isolated and membrane fractions were prepared as described in Bavik et al, J. Biol. Chem. 266:14978–14875 (1991) incorporated by reference. RPE-membrane proteins were then solubilized in phosphate-buffered saline (PBS)(20 mM sodium phosphate, pH 7.2, containing 150 mM NaCl), containing 1% 3-[(3-cholamidopropyl)-dimethylammonio]-1-propane sulfonic acid (CHAPS) at 1 mg of total membrane protein/ml of buffer. Remaining material was removed by ultracentrifugation at 100,000×g for 1 hour. Next, 500 ul aliquots of the solubilized membranes were subjected to gel filtration on a Sepharose 6 column equilibrated in PBS containing 1% CHAPS. The column was operated at a flow rate of 0.2 ml/min and 500 ul fractions collected. Proteins eluted in fractions corresponding to globular proteins of $M_r$ 150,000 to 400,000 were then radiolabelled with $Na^{125}I$ using the well-known Chloramin T procedure. Non-incorporated,$^{125}I$ was removed by gel filtration on Sepahadex G-25 packed in a Pasteur pipette.

Aliquots of the radiolabelled proteins were then diluted in PBS containing 1% CHAPS and 1% bovine serum albumin and subsequently subjected to immunoprecipitation using mAb A52, which specifically binds to p63 (5 ug per incubation) or by using two polyclonal rabbit antisera to p63 (3 ul of serum per incubation) See Bavik et al., J. Biol. Chem. 267:23035–23042 (1992). Non-specific immunoprecipitation was monitored in parallel incubations using an unrelated mAb and preimmune rabbit serum. Fifty ul of a 50% slurry of protein A-Sepharose was added to the incubations for 30 minutes. The beads were subsequently carefully washed with PBS containing 1% CHAPS and the eluted material then prepared for SDS-PAGE analysis, was carried out according to the classic method of Blobel et al. J. Cell. Biol. 67:835–851 (1975).

Referring now to FIG. 1A, autoradiograms of the SDS-PAGE gels showed that both types of reagents reacted with p63, whereas the unrelated mAb or preimmune rabbit serum did not precipitate p63. In all lanes containing immunoprecipitated p63 there was an enrichment of a $M_r$ 32,000 protein. Since both mAb A52 and the rabbit antisera to p63 are highly specific for p63 (See, for example, Bavik et al., J. Biol. Chem. 267:23035–23042 (1992)), it can be concluded that the $M_r$ 32,000 protein (p32) coprecipitated in the aforesaid analysis by binding to p63. The analysis also identified a double band of $M_r$ 50,000–52,000 which precipitated along with p32 and p63 (FIG. 1D, E).

EXAMPLE 2

Figure 1B:
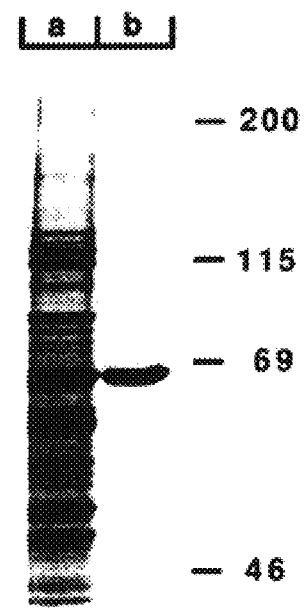
FIG. 1B shows SDS-PAGE analysis of RPE-membrane proteins bound and eluted through an mAb A52 immunoaffinity column, and the presence of p32 in the eluted fraction from the immunoaffinity column.

Experiments were then carried out to identify p32. Advantage was taken of the fact that p32 specifically interacts with p63 as shown supra. Thus, detergent solubilized RPE-membrane proteins were passed over an immunoaffinity column containing mAb A52. Referring now to FIG. 1B, lane b, following a washing procedure, bound proteins were eluted at high pH in a CHAPS-containing buffer, and SDS-PAGE analysis and Coomassie staining of the eluted fractions revealed p63 to be specifically retained and eluted from the immunoaffinity column. Further, a weekly stained band corresponding to p32 could be visualized in the eluate from the A52 column. As shown in FIG. 1B, a comparison of the total protein profile of solubilized RPE membranes and the eluted fraction from the A52 column show that the p32 protein is not efficiently retained therein. However, the appearance of p32 in the eluted fraction from the A52 column, but not in the eluted fraction from the column containing an unrelated Ig, indicate a specific interaction of p32 with p63. This result is consistent with previous immunoprecipitation data, and shows that p32 is complexed to p63 and is retained on the immunoaffinity column due to, this complex formation.

Following identification of p32 as a component of a complex with p63 in RPE-membranes, the p32 protein itself was isolated by SDS-PAGE of eluted fractions of solubilized RPE-membranes from the A52 immunoaffinity column, as set forth below in Example 3.

EXAMPLE 3

RPE-membranes were solubilized in PBS containing 1% CHAPS as set out above and then incubated with mAb A52 Ig coupled to CNBr-activated Sepharose 4B beads (Pharmacia) in a Bio-Rad poly prep column (Bio-Rad) by end-over-end rotation at +4° C. Following a 2 hour incubation, the beads were allowed to settle and the column was quickly washed with 5 column volumes of PBS containing 1% CHAPS. Bound proteins were then eluted with 50 mM triethanolamine buffer (pH 11.2) containing 1% CHAPS. The pH of the eluate was quickly adjusted to 8.0 by the addition of 1M Tris-HCl buffer containing 1% CHAPS. The eluted fractions were subjected to SDS-PAGE, and the separated proteins then visualized by Coomassie Blue staining. A band corresponding to p32 (SDS-PAGE, 32 kDa), was found.

To determine the primary structure of p32, partial amino acid sequence analysis of the isolated protein was undertaken by first cutting out a portion of the aforesaid Coomassie stained band corresponding to approximately 2–5 ug of the 32kDa protein, then lyophilizing the gel piece to dryness. The gel was rehydrated in buffer containing modified trypsin and incubated to generate various peptides for extraction and analysis. A preferred procedure is set forth below in Example 4.

EXAMPLE 4

Coomassie stained bands containing the p32 protein from Example 3 were excised and treated according to Rosenfeld et al. Anal. Biochem. 15:173–179 (1992) with minor modifications. The gel pieces were washed twice for 30 min at 30° C. with 100 ul of 0.2M ammonium bicarbonate buffer containing 50% acetonitrile and thereafter completely dried under a stream of nitrogen. The gel pieces were subsequently rehydrated with 5 ul of 0.2M ammonium bicarbonate buffer containing 0.02% Tween 20 and 0.5 ug of modified trypsin. Trypsin was added from a stock solution prepared in 1 mM HCl. Rehydration was continued by the addition of 5 ul portions of the 0.2M ammonium bicarbonate buffer until the gel pieces rehydrated to their original sizes. The rehydrated gel pieces were then incubated overnight at 30° C. Protease activity was inhibited by the addition of trifluoroacetic acid (TFA) to a final concentration of 1%. The supernatant was recovered and combined with two extracts made with 150 ul of 0.1% TFA in 60% acetonitrile. The organic phase was reduced and the digest was subjected to HPLC using a reverse phase mRPC C2/C18 SC 2.1/10 column operated in a SMART system. The sample was eluted with a gradient of acetonitrile in 0.065% TFA and fractions containing discrete peptides were collected using the automatic peak fractionation option. Five of the identified peptides were selected for amino acid sequence analysis using an ABI 470A sequencer equipped with a model 120A PTH analyzer (applied Biosystems Inc. Foster City, Calif.). The results are set forth below in Table 1.

TABLE 1

Amino acid sequences determinations of five peptides isolated from trypsin digested p32.

| | | |
|---|---|---|
| p321 | L-V-E-A-V-L-A-E-V-L-P-K-P-A-Q-T-V-A | (SEQ ID NO: 1) |
| | (D)[a]       (W)                        (Y) | |
| P322 | Y-S-P-G-W-D-A-K | (SEQ ID NO: 2) |

TABLE 1-continued

Amino acid sequences determinations of
five peptides isolated from trypsin digested p32.

| | | |
|---|---|---|
| P323 | T-P-V-T-N-L-E-T-L-E-D-T-L-Q-A | (SEQ ID NO: 3) |
| P324 | D-V-A-P-F-G-V | (SEQ ID NO: 4) |
| P325 | L-H-T-T-L-L-D-V-T-D-P-Q-S-I | (SEQ ID NO: 5) |

<sup>a</sup>The amino acid residues given within the parentheses are the residues deduced from the cDNA sequence in the same positions.

Protein SEQ ID NOS: 1–5 can be used alone or ligated to hapten by well known methods.

Next, to determine the complete primary structure of p32, four degenerative oligonucleotide mixtures, OM1-OM4, as set forth below in Table 2 were synthesized based on the amino acid sequences of the p321 and p323 sequenced peptides of Table 1. The procedure is as follows in Example 5.

EXAMPLE 5

Four degenerate oligonucleotide mixtures derived from peptides p321 and p323 were synthesized using well-known techniques. The two sense mixtures (OM1 and OM3) were derived from the N-terminal amino acids 1–5 of p321 and 2–6 of p323. The antisense mixtures (OM2 and OM4) were derived from amino acids 12–17 of p321 and 10–15 of p323. All nucleotide mixtures were synthesized with a 4 bp 5' extension and an Eco RI-site for subsequent cloning of the PCR products. The sequences of the oligonucleotide mixtures are set out below in Table 2, and the Eco RI-site is underlined. Positions containing all four bases are marked N.

TABLE 2

OM1:ACGT <u>GAA TTC</u> TN GTN GARGCN GT (SEQ ID NO: 6)
OM2:ACGT <u>GAA TTC</u> AC NGTYTG NGC NGGYTT (SEQ ID NO: 7)
OM3:ACGT <u>GAA TTC</u> CCN GTN ACN AAYYT (SEQ ID NO: 8)
OM4:ACGT <u>GAA TTC</u> GCYTG NARNGTRTCYTC (SEQ ID NO: 9)

Single stranded "complementary" cDNA from reverse transcribed RPE mRNA and four combinations of the above-described degenerate nucleotide mixtures were employed in polymerase chain reactions (PCR) using a standard procedure. Following the amplification procedure, aliquots of the PCR reaction products were analyzed by agarose gel electrophoresis. The procedure is set out below in Example 6.

EXAMPLE 6

To carry out the PCR amplifications, first strand cDNA was synthesized by standard procedures using avian myelostosis virus reverse transcriptase. Twenty ug of total RNA from isolated RPE-cells were used and the reaction was primed with oligo (dT) 15. Aliquots corresponding to 2 ug of total RNA was used in each subsequent PCR reaction. The PCR reactions were performed using a final concentration of 0.5 uM of the oligonucleotide mixtures in a 100 ul reaction. Taq polymerase was used. Following 30 cycles (2 minute at 95° C., 1 minute at 55° C. and 2 minute at 72° C.), aliquots of the reactions were analyzed on 4% GTG agarose gel containing 5 ug/ml of ethidium bromide.

Figure 2:
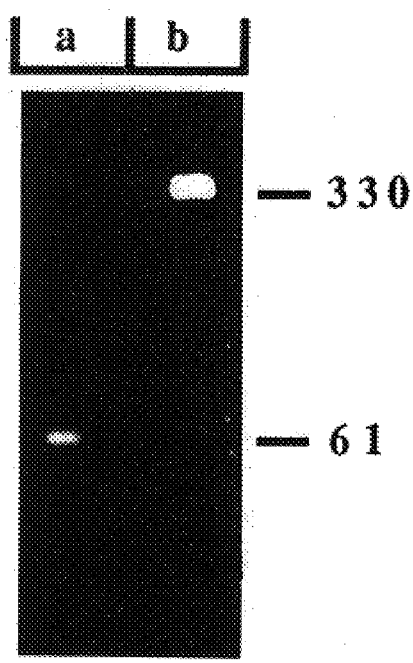
FIG. 2A shows visualization via agarose gel electrophoresis of a 61 bp PCR-amplified fragment using oligonucleotide mixtures OM1 and OM3, both derived from peptide 321 deduced from partial amino acid sequence determination of trypsin digested p32.
FIG. 2B shows visualization of a 330 bp PCR-amplified fragment using oligonucleotide mixtures OM2 and OM3, derived from peptides p323 and p321, respectively, as deduced from partial amino acid sequence determination of trypsin digested p32.
Figure 7:
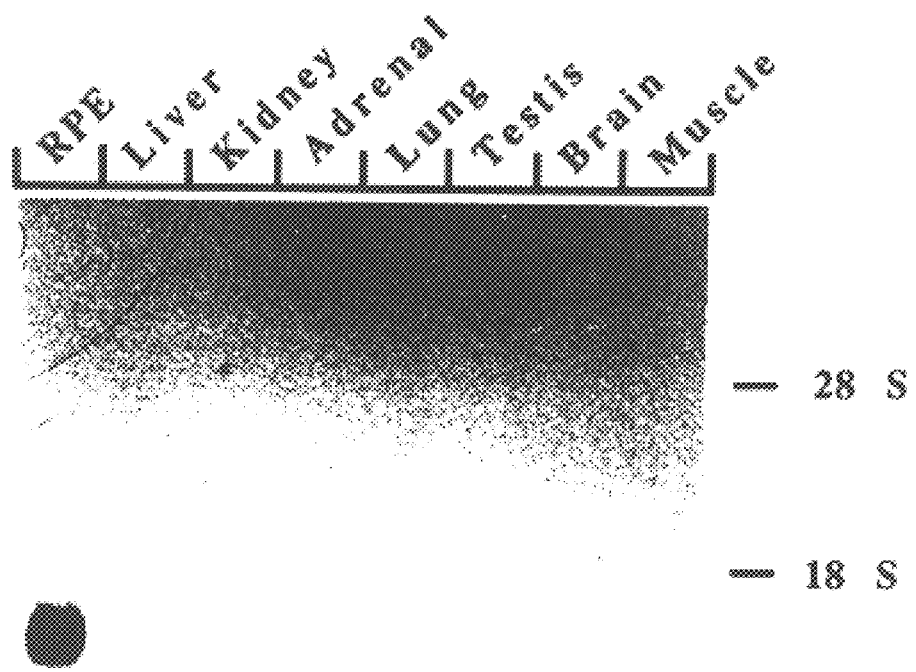
FIG. 7 illustrates the restricted expression of transcripts corresponding to p32.

As shown in FIG. 2A, amplifications using the oligonucleotide mixtures OM1 and OM2, both derived from peptide p321, resulted in an amplified 61 bp fragment. Amplifications using mixtures OM3-OM4 and OM1-OM4 failed to yield any products. Finally, as shown in FIG. 2B, amplification using OM3-OM2 resulted in an amplified 330 bp fragment.

Subsequent sequence analysis of the 61 bp and 330 bp fragments confirmed that cDNA sequences have been amplified which corresponded to the peptide sequences generated in the previous amino acid sequence analysis. Differences between the deduced amino acid sequences from amplified PCR fragments and the generated amino acid sequence of peptide p321 indicates the generation of specific probes suitable for the isolation of full length cDNA clones encoding p32.

To isolate a full length cDNA clone, an RPE-specific lambda ZAP-II cDNA library was screened with the 330 bp fragment as the probe. Five independent lambda clones were isolated from approximately 200,000 clones, and subcloned by in vivo excision. The cDNA clone pλ321 contained the longest insert, (approximately 1.1 Kb), and was selected for use in further studies.

Both strands of pλ321 were fully sequenced with the insert being 1104 bp long, excluding linkers used to prepare the cDNA library. The procedure is set out below in Example 7.

EXAMPLE 7

The amplified products using OM1-OM2 (61 bp) and OM3-OM2 (330 bp) were digested with EcoRI, gel purified and cloned into EcoRI-cut vector pBS. The $^{32}$P-labelled 330 bp fragment was used to screen a RPE-specific λZAP II cDNA library as previously described by Bavik et al., J. Biol. Chem. 267:20540–20546 (1993), incorporated by reference. Five positive λ clones were isolated and the inserts were subcloned in pBluescript by in vivo excision following the manufacturer's instructions. Clone pλ321 contained an insert of 1.1 Kb, and both strands were fully sequenced using Sequenase with T3, T7 or M13 universal primers or with internal primers.

The nucleotide sequence of pλ321 and the predicted amino acid sequence of p32 are shown in FIG. 3 and SEQ ID NO: 10. Nucleotides are numbered on the left and amino acid residues on the right. Amino acid 1 is initial methionine ("Met").

As shown in FIG. 3, the 1.1 kbp insert contains one long open reading frame encoding 318 amino acid residues with a calculated mass of 35,041D. The first methionine residue lies in a good context according to the Kozak rules for transcription initiation and is likely to be the initiation codon. See Kozak, Cell, 44:283–292 (1986). This inference is strengthened by the fact that in vitro translation of synthetic mRNA transcribed from pλ321 gives rise to a $M_r$ 32,000 protein (SDS-PAGE analysis), as set out below, but there is no stop codon in frame in the upstream 35 bp 5'-untranslated region of the cDNA. As also shown in FIG. 3, the 100 bp 3'-untranslated region ends with a putative polyA-tract, and a polyA-signal was identified in the upstream sequence (bp 1104–1110).

The deduced amino acid of pλ321 and the amino acid sequences of the five generated tryptic peptides (Table 1) differ in only 3 positions out of the 62 residues available for a comparison. All 3 differences are found in the peptide p321 but the nucleotide sequence in this region of a second cDNA clone (pλ324) is identical to that of pλ321. This indicates that the amino acid sequence determination of peptide p321 was probably incorrect although it cannot be excluded that the differences are due to the presence of different alleles of p32. These data demonstrate that pλ321 contains the complete coding region of p32.

Again, referring to FIG. 3, a consensus sites for N-linked glycosylation (amino acid residues N-I-T) could be found in the deduced amino acid sequence at position 160–162.

Additionally, it has been found that p32 shows sequence similarities to short-chain alcohol dehydrogenases. Referring now to FIG. 4 a search through the Swissprot protein data base revealed that p32 is structurally related to several previously sequenced proteins. It is most closely related to a mitochondrial matrix dehydrogenase, the D-β-hydroxybutyrate dehydrogenase (BDH) Churchill et al; Biochem. 31:3793–3799 (1992) and shows less but significant similarities to two other proteins, the 3-oxoacyl[acyl carrier protein] reductase from $E.\ coli$ (Rawlings et al., J. Biol. Chem. 267-5751–5754 (1992)) and the human estradiol 17 β-dehydrogenase (Peltoketo et al., FEBS Lett., 239:73–77 (1988) and Leu et al., Mol. Endocrinol. 3:1301-1309 (1989)). All the related proteins fall into the protein superfamily of short-alcohol dehydrogenases. This protein superfamily comprises approximately 50 different proteins (Persson et al, Eur. J. Biochem, 200:537–593 (1991)). The overall sequence homology between p32 and BDH is around 39w. The level of homology to the $E.\ coli$ reductase and to the estradiol 17-β-dehydrogenase is lower (31% and 33%, respectively).

Optimal multiple alignment identified several conserved regions shared by p32 and the most closely related proteins (boxed areas in FIG. 4). The first region involving residues 63–69 (using the numbering in FIG. 4) which displayed the conserved motif G-X-X-X-G-X-G is believed to be the binding site for cofactors NAD, NADP or its reduced forms. Another conserved region is found between residues 148–153 (consensus sequence L-V-N-N-A-G) but no functional characteristics have yet been attributed to that sequence motif. The sequence motif Y-X-X-X-K, thought to be the active site, is the most highly conserved motif in short-chain alcohol dehydrogenases and is present in p32 residues 175–179 See Persson et al., Eur. J. Biochem, 200:537–593 (1991). These similarities demonstrate that p32 exhibits several features of a functional short-chain alcohol dehydrogenase.

As shown in FIG. 5, hydropathy analysis of the amino acid sequence of p32 reveals several hydrophobic stretches, indicating that p32 is a membrane-associated protein. The first 18 amino acids are hydrophobic, and this region has characteristics of a classical signal sequence. However, a consensus site for signal peptidase cleavage could not be identified. See Von Heijne, Nucl. Acid Res., 14:4683–4690 (1986). The amino acids between residues 130 to 150 are hydrophobic and there is a relatively long hydrophobic stretch near the C-terminus of the protein. Thus, p32 displays several hydrophobic regions which are potential membrane spanning segments. In light of the homology to the family of short-chain alcohol dehydrogenases as shown above, it is likely that the central hydrophobic region of p32 (residues 130–150) is not used as a membrane anchor. Instead, both the N-terminal and the C-terminal regions are potential membrane anchoring domains.

To determine the mode of interaction of p32 with membranes, p32 was synthesized by in vitro translation using a reticulocyte lysate system with mRNA transcribed from linearized pλ321. The procedure is set out in Example 8 infra.

EXAMPLE 8

Expression of p32 by in vitro translation

In vitro transcribed mRNA encoding p32 was synthesized from linearized Pλ321 using T7 RNA polymerase. In vitro translation reactions were carried out using nuclease treated rabbit reticulocyte lysate following the manufacturer's instructions. Fifty ng of mRNA was included in each reaction, with or without the addition of dog pancreatic microsomes. To isolate membrane inserted p32, the microsomes were collected by centrifugation at 12,000×g for 10 min at 4° C. The microsomes were carefully resuspended in PBS and recentrifugated.

As shown in FIG. 6, translation in the presence of dog pancreatic microsomes showed that p32 becomes almost quantitatively membrane associated and migrates as a $M_r$ 32,000 species in SDS-PAGE. Translation in the absence of acceptor membranes similarly yields a $M_r$ 32,000 protein. These data indicate that the N-terminal hydrophobic sequence acts as a signal sequence but it is not removed by the signal peptidase, and such supports the previous observation that a consensus site for signal peptidase cleavage could not be identified in the deduced primary sequence.

The tissue expression of p32 was analyzed by Northern blotting analyses using total RNA isolated from bovine RPE, liver, kidney, adrenal, lung, testis, brain and muscle. The procedure is set out in Example 9.

EXAMPLE 9

Northern blot analyses

Twenty ug of total RNA isolated from a number of tissues was electrophoresed on a 1% agarose under denaturing conditions and transferred to a Hybond-N nylon filter. The filter was hybridized with $^{32}$P-labelled full length cDNA encoding p32 under stringent conditions. The details of the isolation of total RNA, hybridization conditions and washing procedure were identical to those previously described in Bavik, et al., J. Biol. Chem. 267:20540–20546 (1993).

Hybridization at high stringency with the 1.1 Kb insert of pλ321 as the probe, revealed abundant expression of transcripts corresponding to p32 only in RPE but not at a detectable level in several other tissues. The size of the major transcript was 1.4 kb but other less abundant transcripts could be visualized after prolonged exposure of the filters both in RPE as well as in other tissues.

EXAMPLE 10

Expression of p32 in COS-cells and enzymatic analysis of the properties of recombinant p32.

p32 was first expressed in COS-cells using a eukaryotic expression vector, and then microsome fractions from transfected cells and control cells were subjected to immunoblotting analysis to verify the expression of p32 at the desired levels, as follows:

Specifically, the EcoRI insert of p λ 321 was cloned into the EcoRI-digested eucaryotic expression vector pSG5. See Green et al., Nucl. Acid Res. 16:39 (1988). COS-cells were maintained in Dulbecco's minimal essential medium supplemented with 10% fetal bovine serum, 2 mM glutamine and antibiotics. The cells were seeded into 60 mm petri dishes ($4 \times 10^5$ cells per dish) and transfected with 5 ug of plasmid per dish using DEAE dextran. Control cells were transfected with equal amounts of the parental vector alone. After treatment with 10% DMSO for 2 minutes, the cells were incubated for 72–96 hours, and then harvested by scraping the dishes with a rubber policeman, and the cells thereafter collected by low speed centrifugation. The collected cell pellets were next resuspended in hypotonic buffer (10 mM Tris-HCl, pH 7.5, containing 1 mM phenyl-methylsufonyl fluoride), put on ice for 20 minutes, and then homogenized using a Dounce homogenator. Unbroken cells and debris were removed by centrifugation (3000×g)for 15 minutes. Microsomes were subsequently collected by ultra-centrifugation at 100,000×g for 1 hour; membrane pellets were stored at −80° C. until further analyzed.

Antisera to p32 were generated by injecting rabbits with p32 (amino acid residues 19–318) expressed as a fusion protein with GST. The bacterial expression vector pGEX 2T was used and the GST-fusion protein was induced and purified, as recommended by the supplier (Pharmacia). Each rabbit received a subcutaneous injection of 75 ug of fusion protein emulsified in Freunds complete adjuvant. The rabbits were boostered with 50 ug of fusion protein emulsified in Freunds incomplete adjuvant every rabbit sera were passed over a column containing GST fusion-protein immobilized on CNBr activated Sepharose beads. Bound Ig was eluted with 0.1M sodium citrate buffer (pH 3.0), containing 0.5M NaCl. To remove Ig to the GST portion of the fusion protein, the eluted Ig was similarly incubated with GST-coupled Sepharose beads and the unbound Ig fraction was used. For immunoblot analysis of the over expressed protein, the Ig was used at a concentration of 1 ug per ml. The details of the immunoblotting procedure are described in detail in Bavik et al., J. Biol. Chem., 267:23035–23042 (1992) the disclosure of which is herein incorporated by reference.

Figure 8A:
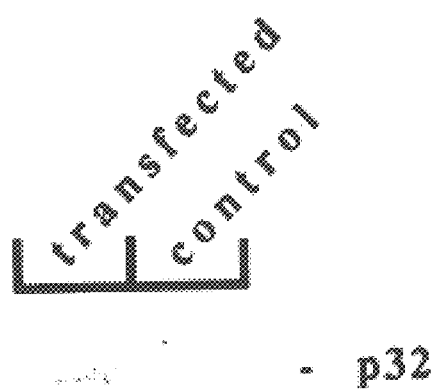
FIG. 8A illustrates expression of p32 in transfected cells for further enzymatic activity analysis of 11-cis retinol dehydrogenase activity.

As shown in FIG. 8A, the above procedure resulted in expression of p32 in cells transfected with the recombinant expression vector, but not in control cells that were mock transfected.

Next, the enzymatic properties of p32 expressed in COS-cells was assayed in a manner similar to that as described in the study of 11-cis-retinol dehydrogenase activity in microsomal fractions of RPE cells. See Saari et al., Anal. Biochem 213:28–13226 (1993).

In particular, the enzymatic activity of p32 was confirmed by incubating the microsomal fractions from the aforementioned transfected cells, and from control cells lacking p32, with varying combinations of the different stereo isomeric substrates, i.e., 11-cis-retinol or all-trans-retinol, in the presence of either cofactor NAD+ or NADP.

To prepare the substrate, 11-cis retinol was synthesized from 11-cis-retinaldehyde using sodium borohydride, as set fourth in Heller et al., J. Biol. Chem. 248:6308–6316 (1973), and stored under argon at 80° C. HPLC analysis confirmed the quantitative reduction of 11-cis-retinaldehyde to 11-cis-retinol, and all manipulations with the retinoids were done under subdued lighting conditions.

To assay for p32 activity in transfected cells, the final concentration of 11-cis-retinol and all-trans-retinol (obtained from Sigma Chemical Co.) in the incubations was reduced to 100 uM. Twenty ug of total membrane protein from COS-cells expressing p32 or from control cells were used in each incubation, and thereafter a 30 minute incubation at 37° C. in the presence or absence of NAD+ or NADP followed. Reaction mixtures were then extracted with n-hexane, and organic phases removed and dried under argon. The dried organic phases were then separately dissolved in ethanol and aliquots were analyzed on a normal phase silica HPLC column developed with n-hexane containing 4% dioxane at 1 ml per minute. See Saari et al. J. Biol. Chem. 257:13329–13333 (1982). Effluent was monitored at 330 nm. Under these conditions, 11-cis-retinaldehyde and 11-cis retinal eluted at 7 minutes and 22.5 minutes, respectively, and all-trans-retinaldehyde and all-trans retinal eluted at 8 minutes and 23 minutes, respectively.

Figure 8B:
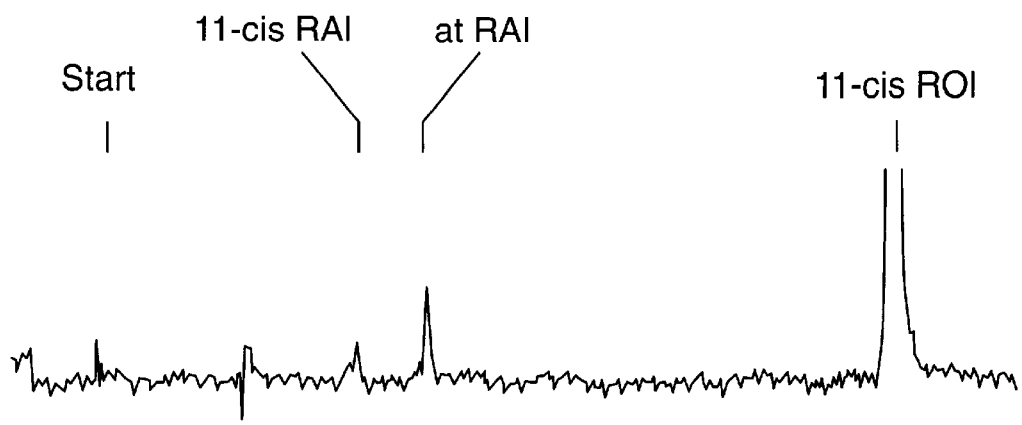
FIG. 8B illustrates the expression of 11-cis retinol dehydrogenase activity in the presence of NAD+ as indicated by the formation of 11-cis retinaldehyde.

As indicated in FIG. 8B, the aforementioned HPLC analysis shows that fractions from transfected cells containing p32 expressed 11-cis-retinol dehydrogenase protein which was active in the presence of NAD+, as indicated by the formation of 11-cis-retinaldehyde. A second peak in the chromatogram is all-trans retinaldehyde; however, control incubations with 11-cis retinaldehyde, in the absence of cellular membranes, show that, under the test procedure employed, a large amount of 11-cis retinaldehyde isomerizes to all-trans retinaldehyde. This indicates that the appearance of all-trans retinaldehyde is due to its generation during the incubation process used and extraction procedures, and is not an enzymatic reaction product. Further, incubations with all-trans retinal with cells containing p32 verify the stereo specificity of the enzyme, as no significant formation of all-trans retinaldehyde is detected.

Figure 8C:
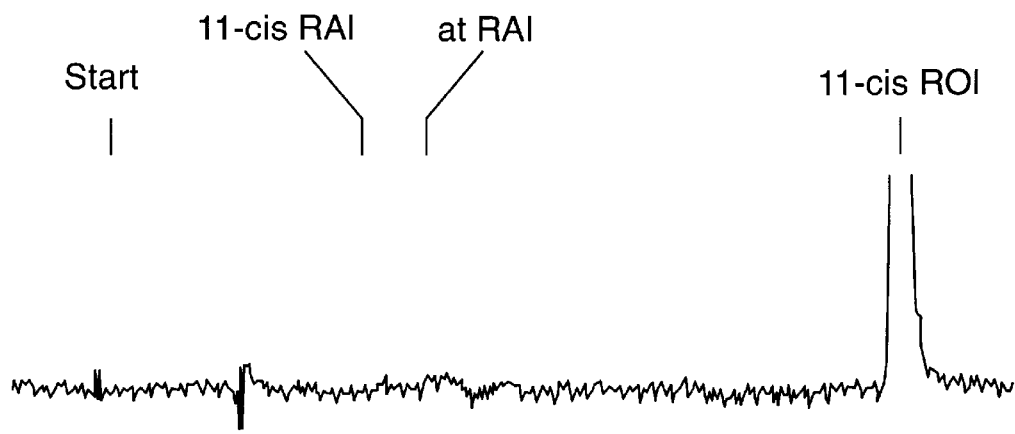
FIG. 8C illustrates the lack of 11-cis-retinol dehydrogenase activity in the presence of cofactor NADP.

As shown in FIG. 8C, p32 is not enzymatically active in the presence of cofactor NADP.

Figure 8D:
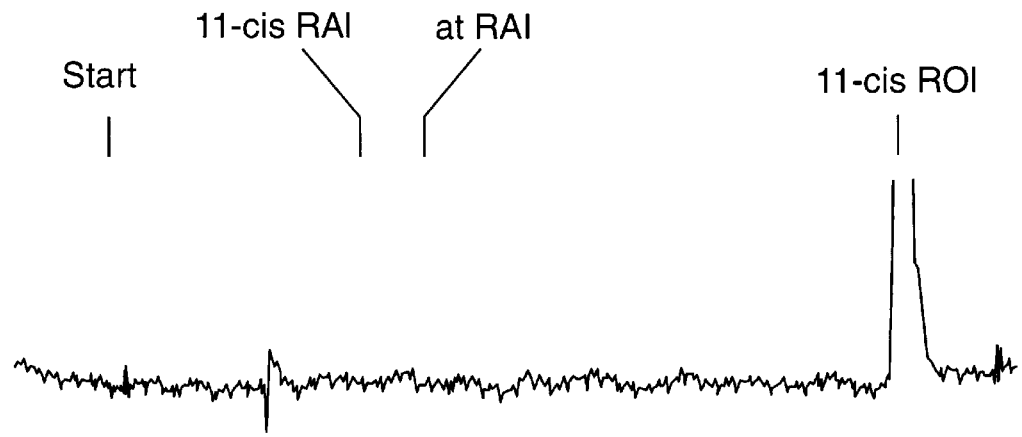
FIG. 8D illustrates control cells not expressing p32 which lack the ability to oxidize 11-cis-retinol into 11-cis-retinaldehyde.

In FIG. 8D assays of the control cells not expressing p32 show that these do not oxidize 11-cis-retinol into 11-cis-retinaldehyde.

Therefore, the above shows conclusively that p32 is a stereo specific 11-cis-retinol dehydrogenase, which relies on NAD+ as its cofactor.

EXAMPLE 11

Following the work described supra, using bovine materials, additional experiments were carried out to isolate and to clone a human sequence.

A cDNA library from human eye, in λgt11 was purchased from a commercial supplier (i.e., Clontech). The bovine cDNA described supra, i.e., SEQ ID NO: 10, was used as a probe. The cDNA was $^{32}$[P] dCTP labelled by random priming to a high specific activity (about $10_9$ cpm/$\mu$g of DNA).

The labelled bovine cDNA was then used to probe the human cDNA library. Conditions were as follows: hybridization in 6× SSC, 0.5% SDS, 5× Denhardt's solution, 25% formamide, at 68° C., with 100 $\mu$/ml of salmon sperm DNA, followed by four washes of 2× SSC, 0.5% SDS, at 65° C., for 30 minutes each, and then a final wash at 2× SSC at 42° C. for 30 minutes.

When a positive cDNA was found, the insert (i.e., the cDNA), was excised following the manufacturer's instructions, and then subcloned into the commercially available vector pBluescript. The sequence of the insert was then determined, using well known methods. The sequence of 1128 nucleotides is set forth at SEQ ID NO: 14. The corresponding amino acid sequence of 318 residues is se forth in SEQ ID NO:15.

EXAMPLE 12

In further experiments, the information described in example 11, supra, was used to study and to analyze bovine neuroretina and murine 10 day embryos. Murine embryos were used because, apart from the general usefulness of the system for studying developmental biology, retinol dehydrogenases are extremely active in development. The model is extrapolatable to human development.

RNA (5–10 μg), was isolated from bovine neuroretinas, or from murine 10 day embryos, using well known techniques. The RNA was mixed in 4 μl of 5× AMVRT buffer, together with 4 μl of dNTPs from 5 mM stock solutions, 2 μl of oligo dT (18mer, at a final concentration of 10 μM), together with 0.5 μl RNAse inhibitor, and 2μl of avian myelostosis virus reverse transcriptase (10U). The final volume was 20 μl. This resulting mixture was incubated at 42° C. for 30 minutes, and then left on ice until used.

PCR was then carried out. In the PCR, two μl of cDNA were used. Primers were designed on the basis of the deduced amino acid sequence for bovine cDNA set forth supra. The following conserved amino acid sequences were noted:

A) Cys Asp Ser Gly Phe Gly
B) Pro Gly Trp Asp Ala
C) Glu Ala Phe Ser Asp
D) His Pro Arg Thr

"A" corresponds to amino acids 36–41 of SEQ ID NO:12. "B" is found at amino acids 283–287 of this sequence. "C" is found at positions 183–187, and "D" at positions 276–279. "Conserved" as used herein refers to conservation between the deduced sequence, the sequence for liver RDH shown by Chai, et al. J. Biol. Chem 270: 3900–3904 (1995), incorporated by reference in its entirety, and Simon, et al, J. Biol. Chem 270: 1107–1112 (1995), also incorporated by reference.

Degenerate oligomers were prepared. In a first set of PCR experiments, degenerate oligos based upon A and B were used as primers, i.e.:

5'- A C G T G A A T T C T G Y G A Y T C N G G N W T Y G G - 3'   (SEQ ID NO:16)

5'- A C G T G A A T T C T T N G C R T C C C C A N C C - 3'   (SEQ ID NO:17)

as forward and reverse primers respectively. The primers were mixed with the two μl of cDNA discussed supra. Conditions were 1 minute of denaturation at 94° C., 1 minute of annealing at 50° C., and two minutes at 72° C., for elongation. This constituted 1 cycle. Twenty-five cycles were carried out.

Following the first PCR, 5 μl samples of PCR product were combined with primers based upon "C" and "D," i.e.:

5'- A C G T G A A T T C G A R G C N T T Y T C N G A - 3'   (SEQ ID NO:18)

5'- A C G T G A A T T C C G N G T N C K N G G R T G - 3'   (SEQ ID NO:19)

as forward and reverse primers, respectively. Conditions were exactly as used in the first set of experiments, except that the annealing temperature was 55° C.

Reaction products were analyzed on 1.5% agarose gels with ethidium bromide. The assumption was that the amplification products should be about 300 base pairs in length. As such, any 300 base pair bands visualized confirmed that the PCR protocol generated products of appropriate size. The experiments were repeated, using 1% low melting point agarose gels, and the PCR products were eluted therefrom. The isolated products were reamplified, using the same protocols, and were cloned into plasmids (TA cloning kit, Invitrogen). The plasmid DNA was prepared from transformants using standard protocols, and then analyzed by restriction digestion, using EcoRI. Any inserts of about 300 base pairs were analyzed further, using vector specific primers. The PCR products are presented in SEQ ID NOS: 20–23 with deduced amino acid sequences being presented as SEQ ID NOS: 24–27. SEQ ID NOS: 20 and 24 correspond to bovine sequences, while all others are murine sequences. In these nucleotide sequences, the first base ("C") is an artifact of the experiment, resulting from cleavage by a restriction endonuclease. Hence, one begins with the second nucleotide base in determining the deduced amino acid sequence. Further, note that sequences corresponding to the degenerate oligos, which would normally be included at the 5' and 3' termini, are not included.

EXAMPLE 13

The PCR product set forth in SEQ ID NO: 19 was then used in further probing experiments.

A murine 8.5 day cDNA library (in λgt10), was screened, using randomly labelled SEQ ID NO: 22, where the hybridization took place in 6× SSC, 0.5% SDS, 5× Denhardts's solution, 50% formamide at 42° C., with 100 μg/ml of salmon sperm DNA, followed by one wash at 2× SSC, 0.5% SDS at 50° C. for 30 minutes. A positive cDNA clone was identified, subcloned into pBluescript, and sequenced. The nucleotide sequence, and deduced amino acid sequence, are set forth as SEQ ID NOS: 28 and 29.

EXAMPLE 14

Following the work described, supra, the human cDNA was used to probe a human genomic library. The probe was prepared by PCR and randomly labelled as described sura.

The primers used in the PCR were derived from the cDNA sequence of SEQ ID NO:11 and were as follows:

Forward primer:
  5'-G C T T C G G G C G C T G T A G T A-3' (SEQ ID NO:30) and
Reverse Primer:
  5'-A A A A C A A T C T C T T G C T G G A A-3'" (SEQ ID NO:31)

PCR was carried out by denaturing at 95° C., followed by annealing at 55° C., and elongation at 72° C. 2-5U of Taq polymerase and 0.2 μM of each primer were used. Thirty cycles were carried out.

The amplified fragment of 1056 bp was isolated, following agarose gel electrophoresis analysis and cloned into vector PCR (commercially available from Invitrogen). This probe was used to screen a human genomic library in λFXII vector, from Stratagene. The manufacturer's instructions were followed to screen approximately 1×10⁶ plaque forming units. 10₆ cpm/ml of hybridization solution was used. Hybridization was carried out overnight with 6× SSC, 0.5% SDS, 5× Denhardt's solution, 50% formamide at 42° C., with 100 μg/ml of salmon sperm DNA, followed by one wash at 1× SSC, 0.1% SDS at 50° C. and a final wash at 0.5× SSC, 0.1% SDS at 650° C. Each wash was for 30 minutes. Several positive plaques were isolated, rescreened, and λDNA prepared, using the glycerol step gradient method described by Sambrook et al. Molecular Cloning, A Laboratory Manual (2d edition, 1989), incorporated by reference.

The isolated genomic clones were sequenced by analyzing fragments obtained following PCR reactions, using 100 mg of genomic λ clones per reaction as templates. To carry out the PCR, different primers, derived from the cDNA sequence of SEQ ID NO:11 were used in two PCR reactions, numbered 'one' and 'two'.

Specifically, the primers used in PCR reaction one were
SEQ ID NO:30, supra (forward primer) and
5'-C T C A G G C T G T C A G A G A A G G C C T-3'
(SEQ ID NO:32) (reverse primer)
The primers used in PCR reaction two were
5'-G A C G A T T T C C A G C G G G T G C-3'
(SEQ ID NO:33) (forward primer) and
SEQ ID NO:31, supra PCR was carried out by denaturing at 95° C., followed by annealing at 55° C. and elongation at 72° C. 2-5U of Taq polymerase and 0.2 μM of each primer was used. Thirty cycles were carried out. The amplified fragments from reactions one and two, were 2.2 kb and 2.5 kb respectively. Each fragment was cloned into vector PCR commercially available from Invitrogen.

Sequence analysis of the cloned fragments using vector specific primers or internal primers, permitted identification of exon-intron boundaries.

Figure 9:
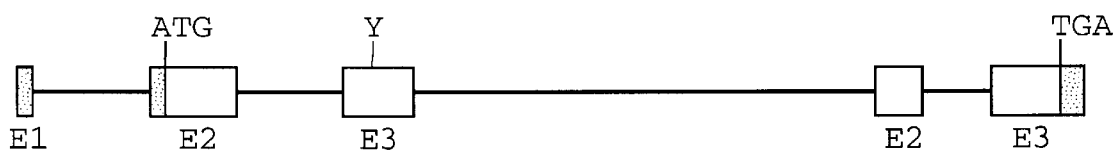
FIG. 9 shows the structure of the human 11-cis-retinol dehydrogenase gene.

The structure of the gene is presented in FIG. 9.

EXAMPLE 15

Studies were carried out to identify the location of the gene on chromosomes.

To do this, high molecular weight DNA was isolated from human leuckoytes, Chinese hamster cells, murine liver cells, and from hamster/human and mouse/human somatic hybrid cell lines. These hybrid cell lines each retained one human chromosome, as well as rodent genomes.

The isolated DNA was digested with Hind III, fractionated on agarose gel via electrophoresis, and then transferred to a nylon filter. These were then probed, using the human cDNA described supra, labelled as described supra.

Slides of chromosomes were prepared from lymphocyte cultures, using art recognized techniques. The λDNA from 3 genomic clones were mixed and labelled with biotinylated 16-dUTP, by Nick translation. A centromere specific probe for human chromosome 12 centromere (obtained from the ATCC, under Accession Number D12Z1), was labelled with fluoro-red-dUTP, following the manufacturer's instructions. Pre-annealing of the probes, pretreatment of the slides, hybridization conditions, signal amplification, and detection, were in accordance with well known techniques. Chromosomes were counter-stained with 4,6 diamino-2-phenyl indole (DAPI), and signal was visualized using a fluorescence microscope.

Analysis of all of these data indicated that the gene for human 11-cis RDH spans more than 4 kilobases, and is divided into 4 coding exons, which range from 165 to 342 base pairs in length. Further, an exon was found in the 5 untranslated region, and the length of the last coding exon has not been established. Introns range in size from 250 base pairs to 1.9 kilobases. FIG. 9 shows this schematically.

Study of exon/intron boundaries showed that all splice donor and acceptor sites follow the well known, canonical GT/AG rule. The Initiation codon and the conserved cofactor binding site are encoded by exon 2, while the active site, with invariant tyrosine residue, is encoded by exon 3. The gene for human 11-cis maps to chromosome 12q13-14.

As shown above, this invention provides a method for the isolation and characterization of a novel protein, p32, which associates with the p63 of RPE. The primary structure of p32 demonstrates that it has all the critical features of a functional short-chain alcohol dehydrogenase including a putative cofactor binding site and essential residues involved in the catalytic mechanism, namely the almost invariant tyrosine containing sequence motif Y-X-X-X-K (Persson et al., Eur. J. Biochem. 200:537–543 (1991)). The restricted tissue expression and the abundance of p32 in RPE indicates that this protein carries out a function which is unique to the RPE. This possibility, and the fact that it forms a complex with p63 which previously has been shown to be a component of the retinoid uptake machinery in RPE-cells (Bavik, et al., J. Biol. Chem. 267:23035–23042 (1992)), shows that the substrate for p32 is a retinoid.

A major metabolic step in retinoid metabolism in RPE-cells is the conversion of 11-cis retinol to 11-cis retinaldehyde. Based on the results obtained hereinabove showing the restricted expression of p32 in the RPE, and the particular biochemical properties of this protein further investigation confirmed that p32 is in fact an 11-cis-retinol dehydrogenase, the enzyme which catalyzes this reaction.

One aspect of the invention is the ability to produce recombinant 11-cis-retinol dehydrogenase. The recombinant enzyme can be used to produce 11-cis-retinaldehyde in levels higher, and in purer form, than would be,available using standard biochemical methodologies. Thus, the isolated nucleic acid molecules of the invention, which include SEQ ID NOS: 10, 14, 20–23, 28 and 29, as well as sequences which have complements which hybridize to the listed sequences, under stringent conditions as well as those nucleic acid molecules which hybridize to SEQ ID NO: 10 under stringent conditions can be used in this context. By the term "stringent conditions" is meant hybridization in 6× SSC, 0.5% SDS, 5× Denhardt's solution at 68° C., with 100 ug/ml of salmon sperm DNA, and a final wash with 0.5–1.0× SSC at 50° C. The term is also used herein to refer to any set of parameters which are at least as stringent as those set forth above. As is well known, equally stringent conditions can be created by changing one parameter to make it less stringent, with another parameter being changed to increase its stringency. Thus, any nucleic acid molecule which fulfills the hybridization criteria set forth herein will be expected to code for p32 or a p32 homologue. These nucleic acid molecules preferably encode mammalian retinol dehydrogenases, such as 11-cis-retinol dehydrogenase. Exemplary, but by no means the only mammalian species included, are human, bovine and murine enzymes. The enzyme may be produced in an in vitro system, such as the one described above, or via transfecting or transforming eukaryotic or prokaryotic cell lines, such as CHO and COS cells or bacterial strains such as E. coli or the yeast strain S.cervisiae with the nucleic acid molecules of the invention. In an especially preferred embodiment, the nucleic acid molecules are contained within an expression vector, operably linked to a promoter. Complementary DNA, or "cDNA" is preferred, but genomic DNA and mRNA can also be used.

The identification of the p32, 11-cis retinol dehydrogenase, as a member of the short-chain alcohol dehydrogenase superfamily is important in view of the retinoid-metabolism which occurs in non-ocular tissues. Studies show that generation of all-trans retinoic acid from all-trans retinol is carried out in a two step process (Posch et al., Biochemistry 30:6224–6230 (1991)). First, retinol is oxidized to retinal by a membrane bound retinol dehydrogenase. In a second step, the retinal is oxidized to retinoic acid. Thus, the oxidation of retinol into retinal, occurring in non-ocular tissues, is similar to the reaction carried out during synthesis of 11-cis retinal from 11-cis retinol in the visual cycle. In light of these similarities, it can be proposed that formation of all-trans retinal from all-trans retinol is carried out by an enzyme which is structurally similar to the p32 11-cis retinol dehydrogenase isolated by this invention. These findings are surprising in contrast to presently held views as it is generally believed that this metabolic step is carried out by members of the medium chain alcohol dehydrogenases. See Duester, Alcohol Clin. Exp. Res. 15:568–572 (1991); Yang et al., Alcohol Clin. Exp. Res. 17:496 (1993) and Zgombic-Knight et al., J. Biol. Chem. 269:6790–6795 (1994). Thus the identification and structural characterization of the p32 11-cis retinol dehydrogenase, provided by this invention also provides a previously unexpected avenue for the isolation and characterization of similar dehydrogenases involved in retinol metabolism is non-ocular tissues.

The p32 protein and nucleic acid encoding therefor and other aspects of this invention are also useful in many other important applications. For example, as it has been shown that p32 is part of an oligomeric protein complex which functions as a membrane receptor for RBP in RPE-cells, the nucleic acid sequence coding for p32 can be used in a phenotypic/genic diagnostic analysis to determine retinoid accumulation, which can lead to retinitis pigmentosa.

Additionally, as shown, p32 possesses 11-cis-retinol dehydrogenase activity, which catalyzes the conversion of 11-cis retinol to 11-cis-retinaldehyde, a major metabolic step in retinoid metabolism in RPE-cells carried out by a membrane bound dehydrogenase. Thus, retinoid accumulation may be directly or indirectly tied to the presence of p32 and/or its activation or inhibition, for example, its complex formation with the RBP receptor p63.

In other applications the effect of potential retinoid drugs for treatment of various diseases on the 11-cis-retinal dehydrogenase activity of p32 may be assayed as such drugs may adversely effect the enzyme, and to thus determine which of the different drugs have limited or no adverse effect on enzyme activity.

Examples of such diseases include those of the eye and also skin disorders such as psoriasis and acne. Certain cancers such as T-cell leukemias may also be tested by retinoid drugs and hence be candidates for assaying p32 activity.

The various known functions of retinoids also suggests that various other retinoid linked pathological conditions may be diagnosed via assays for levels of the p63/p32 receptor complex associated with a particular retinol binding protein. Art recognized techniques may be used, such a immunoassays, and so forth, to determine whether p63/p32 receptor complex levels are too low or too high—i.e., are at variance with a normal level.

Further, as p32 complexes with the p63 component of the retinoid uptake machinery in RPE cells, it may also be used in a therapeutic context, as it is well known that soluble receptors may be used to prevent binding of a protein to its membrane-linked receptor. Thus, a subject characterized by enhanced levels of production of retinol binding protein may be treated via administering an amount of soluble receptor complex or antibody sufficient to inhibit binding of the retinol binding protein or other related molecule to its target, namely, an inhibitor of p32's retinol dehydrogenase activity. Other aspects of the invention will be clear to the skilled artisan and need not be repeated here.

In yet another application, monoclonal and polyclonal antibodies to p32 can be generated, which are useful, inter alia, in monitoring the instance of pathological conditions characterized by aberrant levels of a receptor for retinol binding protein, by binding analysis of the antibody with body fluid or tissue samples. The generation of antibodies to p32 can be accomplished, for example, by using the procedure set out in Bavik et al., J. Biol. Chem. 268:20540–20546 (1993) for the generation of antibodies to p63, including mAb A52.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

As shown above, this invention provides a method for the isolation and characterization of a novel protein, p32, which associates with the p63 of RPE. The primary structure of p32 demonstrates that it has all the critical features of a functional short-chain alcohol dehydrogenase including a putative cofactor binding site and essential residues involved in the catalytic mechanism, namely the almost invariant tyrosine containing sequence motif Y-X-X-X-K (Persson et al., Eur. J. Biochem. 200:537–543 (1991)). The restricted tissue expression and the abundance of p32 in RPE indicates that this protein carries out a function which is unique to the RPE. This possibility, and the fact that it forms a complex with p63 which previously has been shown to be a component of the retinoid uptake machinery in RPE-cells (Bavik, et al., J. Biol. Chem. 267:23035–23042 (1992)), shows that the substrate for p32 is a retinoid.

A major metabolic step in retinoid metabolism in RPE-cells is the conversion of 11-cis retinol to 11-cis retinaldehyde. Based on the results obtained hereinabove showing the restricted expression of p32 in the RPE, and the particular biochemical properties of this protein further investigation confirmed that p32 is in fact an 11-cis-retinol dehydrogenase, the enzyme which catalyzes this reaction.

We claim:

1. An isolated cDNA molecule consisting of a nucleotide sequence which hybridizes, under stringent conditions, to the nucleotide sequence set forth in SEQ ID NO: 10.

2. The isolated nucleic acid molecule of claim 1, wherein the nucleotide sequence of said isolated nucleic acid molecule comprises the nucleotide sequence set forth in SEQ ID NO:10.

3. The isolated nucleic acid molecule of claim 1, wherein the nucleotide sequence of said isolated nucleic acid molecule comprises the nucleotide sequence set forth in SEQ ID NO: 14.

4. An isolated genomic DNA molecule consisting of a nucleotide sequence which encodes the protein set forth in SEQ ID NO:15.

5. An isolated nucleic acid molecule which encodes a boume protein having retinol dehydrogenase activity, whose amino acid sequence consists of the amino acid sequence of the protein encoded by the nucleotide sequence set forth in SEQ ID NO: 10.

6. An isolated nucleic acid molecule which encodes a human protein having retinol dehydrogenase activity, whose amino acid sequence consists of the amino acid sequence set forth in SEQ ID NO: 15.

7. An expression vector comprising the isolated nucleic acid molecule of claim 5, operably linked to a promoter.

8. An expression vector comprising the isolated nucleic acid molecule of claim 6, operably linked to a promoter.

9. A cell line or a bacterial cell strain, transformed or transfected with the expression vector of claim 7.

10. A cell line or a bacterial cell strain, transformed or transfected with the expression vector of claim 8.

11. An isolated nucleic acid molecule whose nucleotide sequence consists of a nucleotide sequence which encodes a human protein having retinol dehydrogenase activity, the complementary sequence of which hybridizes, under stringent conditions, to at least one nucleic acid molecule selected from the group consisting of SEQ ID NO: 20, SEQ ID NO: 21, SEQ ID NO: 22, and SEQ ID NO: 23, and sequences complementary thereto.

12. An isolated nucleic acid molecule which encodes a protein having retinol dehydrogenase activity, comprising a nucleotide sequence selected from the group consisting of SEQ ID NO: 20, SEQ ID NO: 21, SEQ ID NO: 22, and SEQ ID NO: 23.

* * * * *

UNITED STATES PATENT AND TRADEMARK OFFICE
CERTIFICATE OF CORRECTION

PATENT NO. : 5,972,646
DATED : October 26, 1999
INVENTOR(S) : Eriksson et al.

It is certified that error appears in the above-identified patent and that said Letters Patent is hereby corrected as shown below:

Column 9,
Line 39, change "w" to -- % --.

Column 14,
Line 41, change "sura" to -- supra --.
Line 65, change "1056 bp" to -- 1056bp --.

Column 15,
Line 4, change "$10_6$" to -- $10^6$ --.

Column 16,
Line 38, change "be, available" to -- be available --.

Column 44,
Line 2, change "boume" to -- bovine --.
Line 60, change "sequence set" to -- sequence of the proteen encoded by the nucleotide sequence set --.

Signed and Sealed this

Twenty-fifth Day of September, 2001

Attest:

NICHOLAS P. GODICI
Attesting Officer
Acting Director of the United States Patent and Trademark Office

SEQUENCE LISTING (1) GENERAL INFORMATION:

(iii) NUMBER OF SEQUENCES: 31

(2) INFORMATION FOR SEQ ID NO: 1:

(i) SEQUENCE CHARACTERISTICS:
       (A) LENGTH: 18 amino acids
       (B) TYPE: amino acid
       (D) TOPOLOGY: linear (ii) MOLECULE TYPE: protein (xi) SEQUENCE DESCRIPTION: SEQ ID NO: 1:

Leu Val Glu Ala Val Leu Ala Glu Val Leu Pro Lys Pro Ala Gln Thr
                 5                  10                 15
Val Ala (2) INFORMATION FOR SEQ ID NO: 2:

(i) SEQUENCE CHARACTERISTICS:
       (A) LENGTH: 8 amino acids
       (B) TYPE: amino acid
       (D) TOPOLOGY: linear (ii) MOLECULE TYPE: protein (xi) SEQUENCE DESCRIPTION: SEQ ID NO: 2:

Tyr Ser Pro Gly Trp Asp Ala Lys
                 5

(2) INFORMATION FOR SEQ ID NO: 3:

(i) SEQUENCE CHARACTERISTICS:
       (A) LENGTH: 15 amino acids
       (B) TYPE: amino acid
       (D) TOPOLOGY: linear (ii) MOLECULE TYPE: protein (xi) SEQUENCE DESCRIPTION: SEQ ID NO: 3:

Thr Pro Val Thr Asn Leu Glu Thr Leu Glu Asp Thr Leu Gln Ala
                 5                  10                 15

(2) INFORMATION FOR SEQ ID NO: 4:

(i) SEQUENCE CHARACTERISTICS:
       (A) LENGTH: 7 amino acids
       (B) TYPE: amino acid
       (D) TOPOLOGY: linear (ii) MOLECULE TYPE: protein (xi) SEQUENCE DESCRIPTION: SEQ ID NO: 4:

Asp Val Ala Pro Phe Gly Val
                 5

(2) INFORMATION FOR SEQ ID NO: 5:

(i) SEQUENCE CHARACTERISTICS:
       (A) LENGTH: 14 amino acids
       (B) TYPE: amino acid
       (D) TOPOLOGY: linear (ii) MOLECULE TYPE: protein (xi) SEQUENCE DESCRIPTION: SEQ ID NO: 5:

Leu His Thr Thr Leu Leu Asp Val Thr Asp Pro Gln Ser Ile
                5                   10

(2) INFORMATION FOR SEQ ID NO: 6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 6:

ACGTGAATTC TNGTNGARGC NGT                                            23

(2) INFORMATION FOR SEQ ID NO: 7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 7:

ACGTGAATTC ACNGTYTGNG CNGGYTT                                        27

(2) INFORMATION FOR SEQ ID NO: 8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 8:

ACGTGAATTC CCNGTNACNA AYYT                                           24

(2) INFORMATION FOR SEQ ID NO: 9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 9:

ACGTGAATTC GCYTGNARNG TRTCYTC                                        27

(2) INFORMATION FOR SEQ ID NO: 10:

(i) SEQUENCE CHARACTERISTICS:
        (A) LENGTH: 1122 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: p32;11-cis retinol dehydrogenase (xi) SEQUENCE DESCRIPTION: SEQ ID NO:10:

| | | |
|---|---|---|
| AGCTTTCCCC TGAGGAGGTC ACCTGGGCTC CAGCC ATG TGG CTG CCT CTG CAG | | 53 |
| Met Trp Leu Pro Leu Leu | | |
| 5 | | |
| TGC CTG CTG CTG GGT GTC TTG CTC TGG GCA GCA CTG TGG TTG CTC AGG | | 101 |
| Leu Gly Val Leu Leu Trp Ala Ala Leu Trp Leu Leu Arg Asp Arg Gln | | |
| 10 15 20 | | |
| GAC CGG CCA GCC AGC GAT GCC TTT ATC TTC ATC ACC GGC TGT GAC TCG | | 149 |
| Cys Leu Pro Ala Ser Asp Ala Phe Ile Phe Ile Thr Gly Cys Asp Ser | | |
| 25 30 35 | | |
| GGC TTT GGG CGG CTC CTT GCT CTG AGG CTG GAC CAG AGA GGC TTC CGA | | 197 |
| Gly Phe Gly Arg Leu Leu Ala Leu Arg Leu Asp Gln Arg Gly Phe Arg | | |
| 40 45 50 | | |
| GTA CTG GCC AGC TGC CTG ACA CCC TCG GGG GCG GAG GAC CTC CAG CGG | | 245 |
| Val Leu Ala Ser Cys Leu Thr Pro Ser Gly Ala Glu Asp Leu Gln Arg | | |
| 55 60 65 70 | | |
| GTC GCC TCC TCC CGC CTC CAC ACC ACC CTG CTG GAT GTC ACA GAT CCC | | 293 |
| Val Ala Ser Ser Arg Leu His Thr Thr Leu Leu Asp Val Thr Asp Pro | | |
| 75 80 85 | | |
| CAG AGC ATC CGG CAG GCA GTC AAG TGG GTG GAA ACG CAT GTT GGG GAA | | 341 |
| Gln Ser Ile Arg Gln Ala Val Lys Trp Val Glu Thr His Val Gly Glu | | |
| 90 95 100 | | |
| GCA GGG CTT TTT GGT CTG GTG AAT AAT GCT GGT GTG GCT GGC ATC ATT | | 389 |
| Ala Gly Leu Phe Gly Leu Val Asn Asn Ala Gly Val Ala Gly Ile Ile | | |
| 105 110 115 | | |
| GGT CCC ACC CCA TGG CAG ACG CGG GAG GAC TTC CAG CGG GTG CTG AAT | | 437 |
| Gly Pro Thr Pro Trp Gln Thr Arg Glu Asp Phe Gln Arg Val Leu Asn | | |
| 120 125 130 | | |
| GTG AAC ACG CTG GGT CCC ATC GGG GTC ACC CTC GCC CTG CTG CCC CTG | | 485 |
| Val Asn Thr Leu Gly Pro Ile Gly Val Thr Leu Ala Leu Leu Pro Leu | | |
| 135 140 145 150 | | |
| CTG CTG CAG GCC CGG GGC CGA GTG ATC AAC ATC ACC AGT GTC CTT GGC | | 533 |
| Leu Leu Gln Ala Arg Gly Arg Val Ile Asn Ile Thr Ser Val Leu Gly | | |
| 155 160 165 | | |
| CGT CTG GCA GCC AAT GGA GGG GGC TAC TGC GTC TCC AAG TTT GGC CTG | | 581 |
| Arg Leu Ala Ala Asn Gly Gly Gly Tyr Cys Val Ser Lys Phe Gly Leu | | |
| 170 175 180 | | |
| GAG GCC TTC TCT GAC AGC CTG AGG CGA GAT GTG GCT CCT TTT GGG GTA | | 629 |
| Glu Ala Phe Ser Asp Ser Leu Arg Arg Asp Val Ala Pro Phe Gly Val | | |
| 185 190 195 | | |
| CGG GTC TCT ATC GTG GAA CCT GGC TTC TTC CGA ACC CCT GTG ACA AAC | | 677 |
| Arg Val Ser Ile Val Glu Pro Gly Phe Phe Arg Thr Pro Val Thr Asn | | |
| 200 205 210 | | |
| CTG GAA ACT TTG GAG GAC ACC CTG CAG GCC TGC TGG GCA CGG CTG CCT | | 725 |
| Leu Glu Thr Leu Glu Asp Thr Leu Gln Ala Cys Trp Ala Arg Leu Pro | | |
| 215 220 225 230 | | |
| CCA GCC ACA CAG GCC CTC TAT GGG GAG GCC TTC CTC ACC AAA TAC CTG | | 773 |
| Pro Ala Thr Gln Ala Leu Tyr Gly Glu Ala Phe Leu Thr Lys Tyr Leu | | |
| 235 240 245 | | |
| AGA GTG CAG CAA CGT ATC ATG AAC ATG ATC TGT GAT CCG GAC CTG GCC | | 821 |
| Arg Val Gln Gln Arg Ile Met Asn Met Ile Cys Asp Pro Asp Leu Ala | | |
| 250 255 260 | | |
| AAG GTG AGC AGG TGC CTG GAG CAT GCC CTA ACT GCC CGT CAC CCC AGA | | 869 |
| Lys Val Ser Arg Cys Leu Glu His Ala Leu Thr Ala Arg His Pro Arg | | |
| 265 270 275 | | |
| ACC CGC TAC AGC CCA GGC TGG GAT GCC AAG CTG CTC TGG TTG CCA GCC | | 917 |
| Thr Arg Tyr Ser Pro Gly Trp Asp Ala Lys Leu Leu Trp Leu Pro Ala | | |
| 280 285 290 | | |
| TCC TAC TTG CCA GCC AGG CTG GTG GAT GCT GTG CTC GCC TGG GTC CTT | | 965 |
| Ser Tyr Leu Pro Ala Arg Leu Val Asp Ala Val Leu Ala Trp Val Leu | | |
| 295 300 305 310 | | |

```
CCC AAG CCT GCC CAG ACA GTC TAC TAA ATCCAGCCCT CCAGCAAAAG          1012
Pro Lys Pro Ala Gln Thr Val Tyr
                315

ATGGTTGTTC AAGGCAAGGA CTCTGATTTA TTCTGTCCCC TACCCTGGTA CTGCCTGGTG  1072

TGTGGCATAA AACAGTCACT CAATAAATGT ATTATTCAAA ACAAAAAAAA            1122
```

(2) INFORMATION FOR SEQ ID NO: 11:

(i) SEQUENCE CHARACTERISTICS:
        (A) LENGTH: 344 amino acids
        (B) TYPE: amino acid
        (D) TOPOLOGY: linear (ii) MOLECULE TYPE: protein (ix) FEATURE:
        (A) NAME/KEY: Rat D-b-hydroxybutyrate dehydrogenase (rBDH)

(xi) SEQUENCE DESCRIPTION: SEQ ID NO:11:

```
Met Met Leu Ala Ala Arg Leu Ser Arg Pro Leu Ser Gln Leu Pro Gly
              5                  10                  15

Lys Ala Leu Ser Val Cys Asp Arg Glu Asn Gly Thr Arg His Thr Leu
             20                  25                  30

Leu Phe Tyr Pro Ala Ser Phe Ser Pro Asp Thr Arg Arg Thr Tyr Thr
             35                  40                  45

Ser Gln Ala Asp Ala Ala Ser Gly Lys Ala Val Leu Val Thr Gly Cys
 50                  55                  60

Asp Ser Gly Phe Gly Phe Ser Leu Ala Lys His Leu His Ser Lys Gly
 65                  70                  75                  80

Phe Leu Val Phe Ala Gly Cys Leu Leu Lys Glu Gln Gly Asp Ala Gly
             85                  90                  95

Val Arg Glu Leu Asp Ser Leu Lys Ser Asp Arg Leu Arg Thr Ile Gln
            100                 105                 110

Leu Asn Val Cys Asn Ser Glu Glu Val Glu Lys Ala Val Glu Thr Val
            115                 120                 125

Arg Ser Gly Leu Lys Asp Pro Glu Lys Gly Met Trp Gly Leu Val Asn
130                 135                 140

Asn Ala Gly Ile Ser Thr Phe Gly Glu Val Glu Phe Thr Ser Met Glu
145                 150                 155                 160

Thr Tyr Lys Glu Val Ala Glu Val Asn Leu Trp Gly Thr Val Arg Thr
            165                 170                 175

Thr Lys Ser Phe Leu Pro Leu Leu Arg Arg Ala Lys Gly Arg Val Val
            180                 185                 190

Asn Ile Ser Ser Met Leu Gly Arg Met Ala Asn Pro Ala Arg Ser Pro
            195                 200                 205

Tyr Cys Ile Thr Lys Phe Gly Val Glu Ala Phe Ser Asp Cys Leu Arg
210                 215                 220

Tyr Glu Met His Pro Leu Gly Val Lys Val Ser Val Val Glu Pro Gly
225                 230                 235                 240

Asn Phe Ile Ala Ala Thr Ser Leu Tyr Ser Pro Glu Arg Ile Gln Ala
            245                 250                 255

Ile Ala Lys Lys Met Trp Asp Glu Leu Pro Glu Val Val Arg Lys Asp
            260                 265                 270

Tyr Gly Lys Lys Tyr Phe Asp Glu Lys Ile Ala Lys Met Glu Thr Tyr
            275                 280                 285

Cys Asn Ser Gly Ser Thr Asp Ser Ser Val Ile Asn Ala Val Thr
290                 295                 300
```

-continued

```
His Ala Leu Thr Ala Ala Thr Pro Tyr Thr Arg Tyr His Pro Met Asp
305                 310                 315                 320

Tyr Tyr Trp Trp Leu Arg Met Gln Val Met Thr His Phe Pro Gly Ala
            325                 330                 335

Ile Ser Asp Lys Ile Tyr Ile His
            340
```

(2) INFORMATION FOR SEQ ID NO: 12:

(i) SEQUENCE CHARACTERISTICS:
        (A) LENGTH: 327 amino acids
        (B) TYPE: amino acid
        (D) TOPOLOGY: linear (ii) MOLECULE TYPE: protein (ix) FEATURE:
        (A) NAME/KEY: Human estradiol 17-b dehydrogenase (hEDH)

(xi) SEQUENCE DESCRIPTION: SEQ ID NO:12:

```
Ala Arg Thr Val Val Leu Ile Thr Gly Cys Ser Ser Gly Ile Gly Leu
                5                   10                  15

His Leu Ala Val Arg Leu Ala Ser Asp Pro Ser Gln Ser Phe Lys Val
            20                  25                  30

Tyr Ala Thr Leu Arg Asp Leu Lys Thr Gln Gly Arg Leu Trp Glu Ala
        35                  40                  45

Ala Arg Ala Leu Ala Cys Pro Pro Gly Ser Leu Glu Thr Leu Gln Leu
50                  55                  60

Asp Val Arg Asp Ser Lys Ser Val Ala Ala Arg Glu Arg Val Thr
65                  70                  75                  80

Glu Gly Arg Val Asp Val Leu Val Cys Asn Ala Gly Leu Gly Leu Leu
                85                  90                  95

Gly Pro Leu Glu Ala Leu Gly Glu Asp Ala Val Ala Ser Val Leu Asp
            100                 105                 110

Val Asn Val Val Gly Thr Val Arg Met Leu Gln Ala Phe Leu Pro Asp
        115                 120                 125

Met Lys Arg Arg Gly Ser Gly Arg Val Leu Val Thr Gly Ser Val Gly
130                 135                 140

Gly Leu Met Gly Leu Pro Phe Asn Asp Val Tyr Cys Ala Ser Lys Phe
145                 150                 155                 160

Ala Leu Glu Gly Leu Cys Glu Ser Leu Ala Val Leu Leu Leu Pro Phe
                165                 170                 175

Gly Val His Leu Ser Leu Ile Glu Cys Gly Pro Val His Thr Ala Phe
            180                 185                 190

Met Glu Lys Val Leu Gly Ser Pro Glu Glu Val Leu Asp Arg Thr Asp
        195                 200                 205

Ile His Thr Phe His Arg Phe Tyr Gln Tyr Leu Ala His Ser Lys Gln
210                 215                 220

Val Phe Arg Glu Ala Ala Gln Asn Pro Glu Glu Val Ala Glu Val Phe
225                 230                 235                 240

Leu Thr Ala Leu Arg Ala Pro Lys Pro Thr Leu Arg Tyr Phe Thr Thr
                245                 250                 255

Glu Arg Phe Leu Pro Leu Leu Arg Met Arg Leu Asp Asp Pro Ser Gly
            260                 265                 270

Ser Asn Tyr Val Thr Ala Met His Arg Glu Val Phe Gly Asp Val Pro
        275                 280                 285

Ala Lys Ala Glu Ala Gly Ala Glu Ala Gly Gly Ala Gly Pro Gly
290                 295                 300
```

```
Ala Glu Asp Glu Ala Gly Arg Ser Ala Val Gly Asp Pro Glu Leu Gly
305                 310                 315                 320

Asp Pro Pro Ala Ala Pro Gln
                325
```

(2) INFORMATION FOR SEQ ID NO: 13:

(i) SEQUENCE CHARACTERISTICS:
        (A) LENGTH: 244 amino acids
        (B) TYPE: amino acid
        (D) TOPOLOGY: linear (ii) MOLECULE TYPE: protein (ix) FEATURE:
        (A) NAME/KEY:E.coli 3-oxoacyl[acyl carrier protein]reductase (FABG)

(xi) SEQUENCE DESCRIPTION: SEQ ID NO:13:

```
Met Asn Phe Glu Gly Lys Ile Ala Leu Val Thr Gly Ala Ser Arg Gly
                5                  10                  15

Ile Gly Arg Ala Ile Ala Glu Thr Leu Ala Ala Arg Gly Gly Lys Val
                20                  25                  30

Ile Gly Thr Ala Thr Ser Glu Asn Gly Ala Gln Ala Ile Ser Asp Tyr
                35                  40                  45

Leu Gly Ala Asn Gly Lys Gly Leu Met Leu Asn Val Thr Asp Pro Ala
50                  55                  60

Ser Ile Glu Ser Val Leu Glu Lys Ile Arg Ala Glu Phe Gly Glu Val
65                  70                  75                  80

Asp Ile Leu Val Asn Asn Ala Gly Ile Thr Arg Asp Asn Leu Leu Met
                85                  90                  95

Arg Met Lys Asp Glu Glu Trp Asn Asp Ile Ile Glu Thr Asn Leu Ser
                100                 105                 110

Ser Val Phe Arg Leu Ser Lys Ala Val Met Arg Ala Met Met Lys Lys
                115                 120                 125

Arg His Gly Arg Ile Ile Thr Ile Gly Ser Val Val Gly Thr Met Gly
130                 135                 140

Asn Gly Gly Gln Ala Asn Tyr Ala Ala Ala Lys Ala Gly Leu Ile Gly
145                 150                 155                 160

Phe Ser Lys Ser Leu Ala Arg Glu Val Ala Ser Arg Gly Ile Thr Val
                165                 170                 175

Asn Val Val Ala Pro Gly Phe Ile Glu Thr Asp Met Thr Arg Ala Leu
                180                 185                 190

Ser Asp Asp Gln Arg Ala Gly Ile Leu Ala Gln Val Pro Ala Gly Arg
                195                 200                 205

Leu Gly Gly Ala Gln Glu Ile Ala Asn Ala Val Ala Phe Leu Ala Ser
                210                 215                 220

Asp Glu Ala Ala Tyr Ile Thr Gly Glu Thr Leu His Val Asn Gly Gly
225                 230                 235                 240

Met Tyr Met Val
```

(2) INFORMATION FOR SEQ ID NO: 14:

(i) SEQUENCE CHARACTERISTICS:
        (A) LENGTH: 1128 base pairs
        (B) TYPE:nucleic acid
        (C) STRANDEDNESS: single
        (D) TOPOLOGY: linear (ii) MOLECULE TYPE: nucleic acid (ix) FEATURE:
    (A) NAME/KEY: human 11-cis retinol dehydrogenase (xi) SEQUENCE DESCRIPTION: SEQ ID NO: 14:

```
TAAGCTTCGG GCGCTGTAGT ACCTGCCAGC TTTCGCCACA GGAGGCTGCC ACCTGTAGGT    60
CACTTGGGCT CCAGCTATGT GGCTGCCTCT TCTGCTGGGT GCCTTACTCT GGGCAGTGCT   120
GTGGTTGCTC AGGGACCGGC AGAGCCTGCC CGCCAGCAAT GCCTTTGTCT TCATCACCGG   180
CTGTGACTCA GGCTTTGGGC GCCTTCTGGC ACTGCAGCTG GACCAGAGAG GCTTCCGAGT   240
CCTGGCCAGC TGCCTGACCC CCTCCGGGGC CGAGGACCTG CAGCGGGTGG CCTCCTCCCG   300
CCTCCACACC ACCCTGTTGG ATATCACTGA TCCCCAGAGC GTCCAGCAGG CAGCCAAGTG   360
GGTGGAGATG CACGTTAAGG AAGCAGGGCT TTTTGGTCTG GTGAATAATG CTGGTGTGGC   420
TGGTATCATC GGACCCACAC CATGGCTGAC CCGGGACGAT TTCCAGCGGG TGCTGAATGT   480
GAACACAATG GGTCCCATCG GGGTCACCCT TGCCCTGCTG CCTCTGCTGC AGCAAGCCCG   540
GGGCCGGGTG ATCAACATCA CCAGCGTCCT GGGTCGCCTG GCAGCCAATG GTGGGGGCTA   600
CTGTGTCTCC AAATTTGGCC TGGAGGCCTT CTCTGACAGC CTGAGGCGGG ATGTAGCTCA   660
TTTTGGGATA CGAGTCTCCA TCGTGGAGCC TGGCTTCTTC CGAACCCCTG TGACCAACCT   720
GGAGAGTCTG GAGAAAACCC TGCAGGCCTG CTGGGCACGG CTGCCTCCTG CCACACAGGC   780
CCACTATGGG GGGGCCTTCC TCACCAAGTA CCTGAAAATG CAACAGCGCA TCATGAACCT   840
GATCTGTGAC CCGGACCTAA CCAAGGTGAG CCGATGCCTG GAGCATGCCC TGACTGCTCG   900
ACACCCCCGA ACCCGCTACA GCCCAGGTTG GGATGCCAAG CTGCTCTGGC TGCCTGCCTC   960
CTACCTGCCA GCCAGCCTGG TGGATGCTGT GCTCACCTGG GTCCTTCCCA AGCCTGCCCA  1020
AGCAGTCTAC TGAATCCAGC CTTCCAGCAA GAGATTGTTT TTCAAGGACA AGGACTTTGA  1080
TTTATTTCTG CCCCCACCCT GGTACTGCCT GGTGCCTGCC ACAAAATA               1128
```

(2) INFORMATION FOR SEQ ID NO: 15:

(i) SEQUENCE CHARACTERISTICS:
       (A) LENGTH: 318 amino acids
       (B) TYPE: amino acid
       (D) TOPOLOGY: linear (ii) MOLECULE TYPE: protein (ix) FEATURE:
       (A) NAME/KEY: human 11-cis retinol dehydrogenase (xi) SEQUENCE DESCRIPTION: SEQ ID NO: 15:

```
Met Trp Leu Pro Leu Leu Leu Gly Ala Leu Leu Trp Ala Val Leu Trp
                 5                  10                  15

Leu Leu Arg Asp Arg Gln Ser Leu Pro Ala Ser Asn Ala Phe Val Phe
            20                  25                  30

Ile Thr Gly Cys Asp Ser Gly Phe Gly Arg Leu Leu Ala Leu Gln Leu
        35                  40                  45

Asp Gln Arg Gly Phe Arg Val Leu Ala Ser Cys Leu Thr Pro Ser Gly
    50                  55                  60

Ala Glu Asp Leu Gln Arg Val Ala Ser Ser Arg Leu His Thr Thr Leu
65                  70                  75                  80

Leu Asp Ile Thr Asp Pro Gln Ser Val Gln Gln Ala Ala Lys Trp Val
                85                  90                  95

Glu Met His Val Lys Glu Ala Gly Leu Phe Gly Leu Val Asn Asn Ala
                100                 105                 110
```

```
Gly Val Ala Gly Ile Ile Gly Pro Thr Pro Trp Leu Thr Arg Asp Asp
            115                 120                 125

Phe Gln Arg Val Leu Asn Val Asn Thr Met Gly Pro Ile Gly Val Thr
130                 135                 140

Leu Ala Leu Leu Pro Leu Leu Gln Gln Ala Arg Gly Arg Val Ile Asn
145                 150                 155                 160

Ile Thr Ser Val Leu Gly Arg Leu Ala Ala Asn Gly Gly Gly Tyr Cys
                165                 170                 175

Val Ser Lys Phe Gly Leu Glu Ala Phe Ser Asp Ser Leu Arg Arg Asp
                180                 185                 190

Val Ala His Phe Gly Ile Arg Val Ser Ile Val Glu Pro Gly Phe Phe
                195                 200                 205

Arg Thr Pro Val Thr Asn Leu Glu Ser Leu Glu Lys Thr Leu Gln Ala
            210                 215                 220

Cys Trp Ala Arg Leu Pro Pro Ala Thr Gln Ala His Tyr Gly Gly Ala
225                 230                 235                 240

Phe Leu Thr Lys Tyr Leu Lys Met Gln Gln Arg Ile Met Asn Leu Ile
                245                 250                 255

Cys Asp Pro Asp Leu Thr Lys Val Ser Arg Cys Leu Glu His Ala Leu
                260                 265                 270

Thr Ala Arg His Pro Arg Thr Arg Tyr Ser Pro Gly Trp Asp Ala Lys
            275                 280                 285

Leu Leu Trp Leu Pro Ala Ser Tyr Leu Pro Ala Ser Leu Val Asp Ala
            290                 295                 300

Val Leu Thr Trp Val Leu Pro Lys Pro Ala Gln Ala Val Tyr
305                 310                 315

(2) INFORMATION FOR SEQ ID NO:16:

(i) SEQUENCE CHARACTERISTICS:
        (A) LENGTH: 27 base pairs
        (B) TYPE:nucleic acid
        (C) STRANDEDNESS: single
        (D) TOPOLOGY: linear (ii) MOLECULE TYPE: nucleic acid (ix) FEATURE:
        (A) NAME/KEY: PCR primer (xi) SEQUENCE DESCRIPTION: SEQ ID NO:16:

ACGTGAATTC TGYGAYTCNG GNWTYGG                                           27

(2) INFORMATION FOR SEQ ID NO:17:

(i) SEQUENCE CHARACTERISTICS:
        (A) LENGTH: 25 base pairs
        (B) TYPE:nucleic acid
        (C) STRANDEDNESS: single
        (D) TOPOLOGY: linear (ii) MOLECULE TYPE: nucleic acid (ix) FEATURE:
        (A) NAME/KEY: PCR primer (xi) SEQUENCE DESCRIPTION: SEQ ID NO:17:

ACGTGAATTC TTNGCRTCCC CANCC                                             25

(2) INFORMATION FOR SEQ ID NO:18:

(i) SEQUENCE CHARACTERISTICS:
        (A) LENGTH: 24 base pairs
```

(B) TYPE:nucleic acid
(C) STRANDEDNESS: single
(D) TOPOLOGY: linear (ii) MOLECULE TYPE: nucleic acid (ix) FEATURE:
(A) NAME/KEY: PCR primer (xi) SEQUENCE DESCRIPTION: SEQ ID NO:18:

ACGTGAATTC GARGCNTTYT CNGA                                          24

(2) INFORMATION FOR SEQ ID NO:19:

(i) SEQUENCE CHARACTERISTICS:
(A) LENGTH: 24 base pairs
(B) TYPE:nucleic acid
(C) STRANDEDNESS: single
(D) TOPOLOGY: linear (ii) MOLECULE TYPE: nucleic acid (ix) FEATURE:
(A) NAME/KEY: PCR primer (xi) SEQUENCE DESCRIPTION: SEQ ID NO:19:

ACGTGAATTC CGNGTNCKNG GRTG                                          24

(2) INFORMATION FOR SEQ ID NO: 20:

(i) SEQUENCE CHARACTERISTICS:
(A) LENGTH: 262 base pairs
(B) TYPE:nucleic acid
(C) STRANDEDNESS: single
(D) TOPOLOGY: linear (ii) MOLECULE TYPE: nucleic acid (ix) FEATURE:
(A) NAME/KEY: PCR clone 194

(xi) SEQUENCE DESCRIPTION: SEQ ID NO: 20:

CTCTCTCAGA AGGGAGCTCT CCTACTTCGG AGTGAAGGTG GCTATGATTG AGCCTGGTTA    60

CTTTGTTACC AATATGACCC AAGATGAGGG TTTTATTGGA TACCTCCAGG CATTGTGGAA   120

CCGGGCCAGC CCAGAGCTGA AGAACTCTA TGGAGAAAAC TTCCCTGCTG ACTTCTTGAA    180

GACATTGAGT TTACTGAAAC CACGGTGGAC TCAGAATCTG TCCTTGGTGA CCGACTGCAT   240

GGAGCACGCC CTGACTGCCT GC                                          262

(2) INFORMATION FOR SEQ ID NO:21:

(i) SEQUENCE CHARACTERISTICS:
(A) LENGTH: 262 base pairs
(B) TYPE:nucleic acid
(C) STRANDEDNESS: single
(D) TOPOLOGY: linear (ii) MOLECULE TYPE: nucleic acid (ix) FEATURE:
(A) NAME/KEY: PCR clone 207

(xi) SEQUENCE DESCRIPTION: SEQ ID NO:21:

CTCCCTCAGG AGGGGGCTCT CCTACTTTGG GGTGAAGGTG GCTATTATAG AGCCTGGCTT    60

CTTCCTGACC GGTGTGACCA GTAGTGCCAG ATTATGCTCA AATACCCAGA TGCTGTGGGA   120

CCAGACCAGC TCAGAAAATCA GGGAGATCTA TGGCGAGAAG TACCTGGCAT CCTATCTGAA  180

AAGGCTAAAC GAATTGGACA AGAGGTGCAA CAAGGACCTG TCTTTGGTGA CTGACTGCAT   240

```
GGAGCATGCT CTGACTGCCT GC                                               262

(2) INFORMATION FOR SEQ ID NO:22:

(i) SEQUENCE CHARACTERISTICS:
        (A) LENGTH: 265 base pairs
        (B) TYPE:nucleic acid
        (C) STRANDEDNESS: single
        (D) TOPOLOGY: linear (ii) MOLECULE TYPE: nucleic acid (ix) FEATURE:
        (A) NAME/KEY: PCR clone 200

(xi) SEQUENCE DESCRIPTION: SEQ ID NO:22:

CAGCCTGAGG CGGGACATGG CTCCGTTCGG AGTACAAGTC TCCATTGTGG AGCCTGGCTT       60

CTTTCGAACC CCTGTGACCA ACCTGGAGAG TCTGGAGAGC ACCCTGAAGG CTTGTTGGGC      120

CCGGCTACCT CCAGCTATAC AGGCCCACTA CGGGGAGGCC TTCCTCGATA CTCATCTTCG     180

AGTACAGCGC CGCATCATGA ACCTGATCTG TGACCCAGAA CTAACGAAGG TGACCAGCTG    240

CCTGGAGCAT GCCCTGACTG CTCGC                                          265

(2) INFORMATION FOR SEQ ID NO:23:

(i) SEQUENCE CHARACTERISTICS:
        (A) LENGTH: 265 base pairs
        (B) TYPE:nucleic acid
        (C) STRANDEDNESS: single
        (D) TOPOLOGY: linear (ii) MOLECULE TYPE: nucleic acid (ix) FEATURE:
        (A) NAME/KEY: PCR clone 215

(xi) SEQUENCE DESCRIPTION: SEQ ID NO:23:

CAGCCTGAGG CGAGATGTGG CTCCTTTTGG GGTACGGGTC TCTATCGTGG AACCTGGCTT       60

CTTCCGAACC CCTGTGACAA ACCTGGAAAC TTTGGAGGGC ACCCTGCAGG CCTGCTGGGC     120

ACGGCTGCCT CCAGCCACAC AGGCCCTCTA TGGGGAGGCC TTCCTCACCA AATACCTGAG    180

AGTGCAGCAA CGTATCATGA ACATGATCTG TGATCCGGAC CTGGCCAAGG TGAGCAGGTG   240

CCTGGAGCAT GCCCTAACTG CCCGT                                         265

(2) INFORMATION FOR SEQ ID NO:24:

(i) SEQUENCE CHARACTERISTICS:
        (A) LENGTH: 87 amino acids
        (B) TYPE: amino acid
        (D) TOPOLOGY: linear (ii) MOLECULE TYPE: protein (ix) FEATURE:
        (A) NAME/KEY:  PCR clone 194

(xi) SEQUENCE DESCRIPTION: SEQ ID NO:24 :

Ser Leu Arg Arg Glu Leu Ser Tyr Phe Gly Val Lys Val Ala Met Ile
                 5                  10                  15

Glu Pro Gly Tyr Phe Val Thr Asn Met Thr Gln Asp Glu Gly Phe Ile
             20                  25                  30

Gly Tyr Leu Gln Ala Leu Trp Asn Arg Ala Ser Pro Glu Leu Lys Glu
         35                  40                  45

Leu Tyr Gly Glu Asn Phe Pro Ala Asp Phe Leu Lys Thr Leu Ser Leu
```

```
                50              55              60
Leu Lys Pro Arg Trp Thr Gln Asn Leu Ser Leu Val Thr Asp Cys Met
65                  70                  75                  80

Glu His Ala Leu Thr Ala Cys
                85
```

(2) INFORMATION FOR SEQ ID NO:25:

(i) SEQUENCE CHARACTERISTICS:
        (A) LENGTH:87 amino acids
        (B) TYPE: amino acid
        (D) TOPOLOGY: linear (ii) MOLECULE TYPE: protein (ix) FEATURE:
        (A) NAME/KEY: PCR clone 207

(xi) SEQUENCE DESCRIPTION: SEQ ID NO:25:

```
Ser Leu Arg Arg Gly Leu Ser Tyr Phe Gly Val Lys Val Ala Ile Ile
                5               10              15

Glu Pro Gly Phe Phe Leu Thr Val Thr Ser Ser Ala Arg Leu Cys
                20              25              30

Ser Asn Thr Gln Met Leu Trp Asp Gln Thr Ser Ser Glu Ile Arg Glu
            35              40              45

Ile Tyr Gly Glu Lys Tyr Leu Ala Ser Tyr Leu Lys Arg Leu Asn Glu
50              55              60

Leu Asp Lys Arg Cys Asn Lys Asp Leu Ser Leu Val Thr Asp Cys Met
65                  70                  75                  80

Glu His Ala Leu Thr Ala Cys
                85
```

(2) INFORMATION FOR SEQ ID NO:26 :

(i) SEQUENCE CHARACTERISTICS:
        (A) LENGTH: 88 amino acids
        (B) TYPE: amino acid
        (D) TOPOLOGY: linear (ii) MOLECULE TYPE: protein (ix) FEATURE:
        (A) NAME/KEY: PCR clone 200

(xi) SEQUENCE DESCRIPTION: SEQ ID NO:26 :

```
Ser Leu Arg Arg Asp Met Ala Pro Phe Gly Val Gln Val Ser Ile Val
                5               10              15

Glu Pro Gly Phe Phe Arg Thr Pro Val Thr Asn Leu Glu Ser Leu Glu
            20              25              30

Ser Thr Leu Lys Ala Cys Trp Ala Arg Leu Pro Pro Ala Ile Gln Ala
            35              40              45

His Tyr Gly Glu Ala Phe Leu Asp Thr His Leu Arg Val Gln Arg Arg
50              55              60

Ile Met Asn Leu Ile Cys Asp Pro Glu Leu Thr Lys Val Thr Ser Cys
65                  70                  75                  80

Leu Glu His Ala Leu Thr Ala Arg
                85
```

(2) INFORMATION FOR SEQ ID NO:27:

(i) SEQUENCE CHARACTERISTICS:
        (A) LENGTH: 88 amino acids
        (B) TYPE: amino acid (D) TOPOLOGY: linear (ii) MOLECULE TYPE: protein (ix) FEATURE:
   (A) NAME/KEY: PCR clone 215

(xi) SEQUENCE DESCRIPTION: SEQ ID NO:27:

```
Ser Leu Arg Arg Asp Val Ala Pro Phe Gly Val Arg Val Ser Ile Val
              5                  10                  15

Glu Pro Gly Phe Phe Arg Thr Pro Val Thr Asn Leu Glu Thr Leu Glu
             20                  25                  30

Gly Thr Leu Gln Ala Cys Trp Ala Arg Leu Pro Pro Ala Thr Gln Ala
             35                  40                  45

Leu Tyr Gly Glu Ala Phe Leu Thr Lys Tyr Leu Arg Val Gln Gln Arg
         50                  55                  60

Ile Met Asn Met Ile Cys Asp Pro Asp Leu Ala Lys Val Ser Arg Cys
65                  70                  75                  80

Leu Glu His Ala Leu Thr Ala Arg
             85
```

(2) INFORMATION FOR SEQ ID NO:28:

(i) SEQUENCE CHARACTERISTICS:
      (A) LENGTH: 563 base pairs
      (B) TYPE: nucleic acid
      (C) STRANDEDNESS: single
      (D) TOPOLOGY: linear (ii) MOLECULE TYPE: nucleic acid (ix) FEATURE:
      (A) NAME/KEY: clone ME207.

(xi) SEQUENCE DESCRIPTION: SEQ ID NO:28:

```
GAGGCGTTCT CGGACTCCCT CAGGAGGGGG CTCTCCTACT TTGGGGTGAA GGTGGCTATT    60
ATAGAGCCTG GCTTCTTCCT GACCGGTGTG ACCAGTAGTG CCAGATTATG CTCAAATACC   120
CAGATGCTGT GGGACCAGAC CAGCTCAGAA ATCAGGGAGA TCTATGGCGA GAAGTACCTG   180
GCATCCTATC TGAAAAGGCT AAACGAATTG GACAAGAGGT GCAACAAGGA CCTGTCTTTG   240
GTGACTGACT GCATGGAGCA TGCTCTGACT GCCTGCCACC CTCGCACGCG ATACTCAGCT   300
GGCTGGGATG CTAAGCTCTT CTACCTCCCC TTGAGCTACC TGCCTACCTT TCTTGTGGAT   360
GCCCTTCTCT ATTGGACTTC CCTGAAGCCT GAGAAAGCCC TCTGACGTGT TCACCTATGT   420
GCATACCTGG GGAGATGTAG GTAGAGTTTG AGAGAGAGAA TATTTAGGGG AAATTTGGAG   480
GGTTGAGGGA GGGAGTTTAT TACTCTGGGG TTCAGTCAAC ACACTTCATC TCATTAATTC   540
TCCTATGACA CTACTGAATA CTG                                           563
```

(2) INFORMATION FOR SEQ ID NO:29:

(i) SEQUENCE CHARACTERISTICS:
      (A) LENGTH: 134 amino acids
      (B) TYPE: amino acid
      (D) TOPOLOGY: linear (ii) MOLECULE TYPE: protein (ix) FEATURE:
      (A) NAME/KEY: clone ME207

(xi) SEQUENCE DESCRIPTION: SEQ ID NO:29:

```
Glu Ala Phe Ser Asp Ser Leu Arg Arg Gly Leu Ser Tyr Phe Gly Val
              5                  10                  15
```

-continued

```
Lys Val Ala Ile Ile Glu Pro Gly Phe Phe Leu Thr Gly Val Thr Ser
         20                  25                  30

Ser Ala Arg Leu Cys Ser Asn Thr Gln Met Leu Trp Asp Gln Thr Ser
         35                  40                  45

Ser Glu Ile Arg Glu Ile Tyr Gly Glu Lys Tyr Leu Ala Ser Tyr Leu
     50                  55                  60

Lys Arg Leu Asn Glu Leu Asp Lys Arg Cys Asn Lys Asp Leu Ser Leu
65                   70                  75                  80

Val Thr Asp Cys Met Glu His Ala Leu Thr Ala Cys His Pro Arg Thr
             85                  90                  95

Arg Tyr Ser Ala Gly Trp Asp Ala Lys Leu Phe Tyr Leu Pro Leu Ser
             100                 105                 110

Tyr Leu Pro Thr Phe Leu Val Asp Ala Leu Leu Tyr Trp Thr Ser Leu
         115                 120                 125

Lys Pro Glu Lys Ala Leu
         130
```

(2) INFORMATION FOR SEQ ID NO:30:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: nucleic acid (ix) FEATURE:
        (A) NAME/KEY: forward primer (xi) SEQUENCE DESCRIPTION: SEQ ID NO:30:

```
GCTTCGGGCG CTGTAGTA                                                18
```

(2) INFORMATION FOR SEQ ID NO:31:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: nucleic acid (ix) FEATURE:
        (A) NAME/KEY: Reverse primer (xi) SEQUENCE DESCRIPTION: SEQ ID NO:31:

```
AAAACAATCT CTTGCTGGAA                                              20
```